(12) United States Patent
Sanderson et al.

(10) Patent No.: US 6,915,714 B2
(45) Date of Patent: Jul. 12, 2005

(54) AUTOMATED SAMPLE COLLECTION WORKSTATION

(75) Inventors: Adrian Ronald Sanderson, Durham, NC (US); Phillip William Waters, Durham, NC (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 10/275,048

(22) PCT Filed: May 1, 2001

(86) PCT No.: PCT/US01/13941

§ 371 (c)(1),
(2), (4) Date: Oct. 31, 2002

(87) PCT Pub. No.: WO01/84108

PCT Pub. Date: Nov. 8, 2001

(65) Prior Publication Data

US 2003/0226391 A1 Dec. 11, 2003

Related U.S. Application Data

(60) Provisional application No. 60/201,004, filed on May 1, 2000.

(51) Int. Cl.[7] ................................................. G01N 1/04
(52) U.S. Cl. .................... 73/863.01; 73/863.22
(58) Field of Search .................... 73/863.01, 863.02, 73/863.03, 863.31, 863.23, 863.22, 865.5; 422/100

(56) References Cited

U.S. PATENT DOCUMENTS

| | | | |
|---|---|---|---|
| 2,307,602 A | | 1/1943 | Barnes et al. |
| 3,687,175 A | * | 8/1972 | Babey ..................... 73/863.32 |
| 4,199,974 A | | 4/1980 | Fryberger et al. |
| 5,500,067 A | * | 3/1996 | Jenkner ..................... 156/146 |
| 2003/0230488 | * | 12/2003 | Lee et al. .................. 204/453 |

FOREIGN PATENT DOCUMENTS

| | | |
|---|---|---|
| GB | 841 698 A | 7/1960 |
| WO | WO 99 26464 A | 6/1999 |

* cited by examiner

Primary Examiner—Hezron Williams
Assistant Examiner—Nashmiya Fayyaz
(74) Attorney, Agent, or Firm—Robert J. Smith

(57) ABSTRACT

An automated sealing assembly for use in an automated sample collection workstation includes a lower clamping plate, an upper clamping plate movable with respect to the lower clamping plate and adapted for sealable engagement with the lower clamping plate, and a clamping drive assembly including a track plate having a track, an axle support, an axle supported by the axle support, a bracket connected to the upper clamping plate and to the axle, the bracket movably and rotatably supported in the track and pivotable about the axle, a motor, and a drive member powered by the motor and adapted to move the bracket along the track.

5 Claims, 38 Drawing Sheets

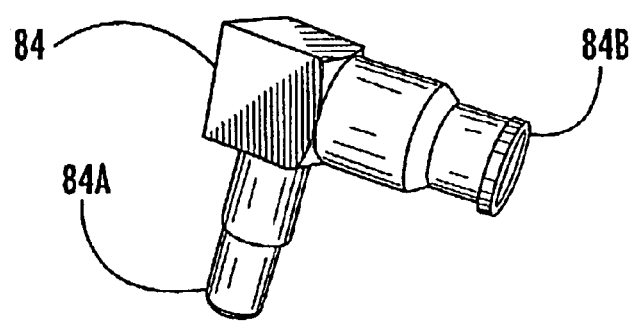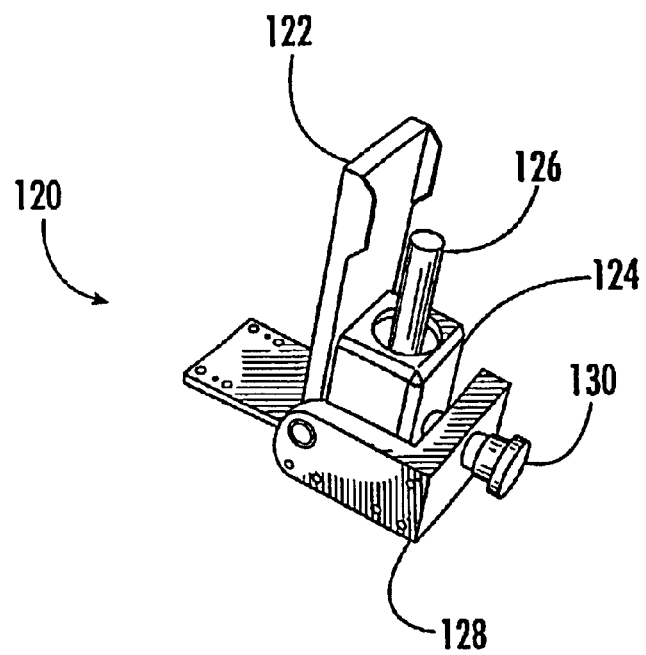
FIG. 16.

AUTOMATED SAMPLE COLLECTION WORKSTATION

This application is filed under 35 U.S.C. §371 as the United States National Phase Application of International Application No. PCT/US01/13941 filed May 1, 2001 claiming priority from U.S. Provisional Application No. 60/201,004 filed May 1, 2000, the disclosures of which are incorporated herein by reference in their entirety.

TECHNICAL FIELD

The present invention is directed generally to the field of sample collection and assaying and, more particularly, to automation of sample collection and preparation procedures.

BACKGROUND ART

Sample preparation and collection tasks are performed in a wide variety of research and testing procedures. As one examples, sampling tasks are performed in conjunction with research relating to pharmaceutical aerosol and powder drug delivery. A popular instrument utilized in this area by those skilled in the art in performing analytical assays is the particle sizing impactor. One specific type of impactor is the multi-stage cascade impactor. The cascade impactor relies on inertial impaction for characterizing aerodynamic particle size distribution of Metered Dose Inhaler (MDI) and Metered Dose Powdered Inhaler (MDPI) products. Such an instrument is useful in that all aerosols can be classified by extensive experimental proofs and empirical verification. Once certain properties of the examined aerosol are known, the cascade impactor can enable comprehensive aerosol definition.

Referring to FIG. 1, a cascade impactor generally designated I typically is constructed of eight to ten classification stages ST that enable, for example, classification of aerosols ranging from 10 to 0.4 :m at 28.3 lpm. In FIG. 1, cascade impactor I includes a stage zero $ST_0$, stages $ST_1$–$ST_7$, a final filter 16, a base element 17, and an inlet cone 18. Each stage ST consists of a jet plate 12 and a stainless steel impaction disc 14 (see FIGS. 10 and 32) or filtration media substrate. Filter 16 collects all particles smaller than 0.4 :m. Pre-separators and other special accessories can be added to allow the cascade impactor to operate at higher flowrates to enable collection of submicron particulate. In FIG. 1, for example, inlet cone 18 is provided for testing of aerosols. A pre-separator 21 (see FIG. 31) would be substituted for inlet cone 18 when dry powders are to be tested. At each stage ST, an aerosol or powder stream passes through the jets of jet plate 12 and around the impaction disc 14. Entrained particles with enough inertia settle upon the impaction surfaces, while smaller particles remain entrained to be deposited upon subsequent stages ST. High jet velocities enable smaller particles to be characterized efficiently. The aerodynamic diameter of the collected aerosol depends upon the jet orifice velocity within each stage ST, the distance between the jets and impaction surface, and the collection characteristics of the preceding jet stage ST.

As is known by those skilled in the art, instruments such as cascade impactor I are employed as part of time-consuming and tedious manual assay procedures. In a typical manual assay, the cascade impaction test includes the following major tasks. Cascade impactor I is assembled and then dosed with the product to be tested. After dosing, cascade impactor I is separated into its individual components. Each stage ST is rinsed with a solvent, and the resulting sample consisting of solvent and particles carried thereby are funneled into a collection container such as a laboratory flask. Additional solvent is then added to dilute the sample to the appropriate volume. The diluted sample is then mixed and assayed by appropriate analytical equipment such as a high-pressure liquid chromatography (HPLC) device.

The desire by those skilled in the art to ameliorate the time and effort required to perform such testing led to the development of the present invention.

DISCLOSURE OF THE INVENTION

Accordingly, the present invention provides a sealing assembly for use in an automated rinsing and sample collection workstation. The sealing assembly comprises a lower clamping plate, an upper clamping plate, and a clamping drive assembly. The upper clamping plate is movable with respect to the lower clamping plate and is adapted for sealable engagement with the lower clamping plate. The clamping drive assembly includes a track plate having a track, an axle support, an axle supported by the axle support, and a bracket connected to the upper clamping plate and to the axle. The bracket is movably and rotatably supported in the track and pivotable about the axle. The clamping drive assembly also includes a motor and a drive member powered by the motor. The drive member is adapted to move the bracket along the track.

According to another embodiment of the present invention, the sealing assembly includes a deck, a lower clamping plate mounted on the deck, and an upper clamping plate movable with respect to the lower clamping plate and adapted for sealable engagement with the lower clamping plate. A throat fixture is mounted on the deck and rotatable onto the lower clamping plate.

According to further embodiment of the present invention, the sealing assembly includes a lower clamping plate and an upper clamping plate. The upper clamping plate is movable with respect to the lower clamping plate and is adapted for sealable engagement with the lower clamping plate. Also provided is an impactor flow unit fixture such as a pre-separator fixture or an inlet cone fixture. The impactor flow unit fixture includes an upper portion and a lower portion. The upper portion is mounted to the upper clamping plate and the lower portion mounted to the lower clamping plate.

The present invention also provides a solvent flow-through system for use in an automated rinsing and sample collection workstation. The system comprises a sealing assembly, a sampling module, a plurality of pairs of metering pumps, and a plurality of multi-position valves. Each valve communicates with a corresponding one of the pairs of metering pumps, and adapted to transfer a fluid to and from the metering pumps, the sealing assembly and the sampling module.

The present invention further provides a sampling module for use in an automated rinsing and sample collection workstation. The sampling module comprises a guide plate having a track disposed along a first axis, a first bracket movably supported in the track, a first motor, and a first drive member powered by the first motor and adapted to move the first bracket along the track. A guide member is movable with the first bracket. Also provided are a second bracket supported by the guide member and movable along the guide member along a second axis, a second motor, and a second drive member powered by the second motor and adapted to move the second bracket along the guide member.

The present invention additionally provides a pump calibration system for use in an automated rinsing and sample collection workstation. The calibration system comprises a balance, a sampling module including a sampling needle, an adjustable metering pump communicating with the sampling needle, and a reservoir removably disposed on the balance.

The present invention still further provides an automated rinsing and sample collection workstation. The workstation comprises a sealing assembly, a sampling module including a sampling needle, and a solvent flow-through system. The solvent flow-through system includes a pump and valve which communicate with the sealing assembly and the sampling needle. The workstation can also include a pump calibration system communicating with the solvent flow-through system.

In addition, the present invention provides a method for rinsing and collecting particulate samples from a particulate testing device. A sealing assembly is provided and includes a lower clamping plate, an upper clamping plate movable in relation to the lower clamping plate, and a plurality of fixtures. A plurality of particle-containing components from a particulate test device are installed onto corresponding fixtures of the sealing assembly. The upper clamping plate is caused to engage the lower clamping plate, whereby the upper and lower clamping plates cooperate with the fixtures to define a plurality of separate rinsing chambers in which corresponding particle-containing components are disposed. Solvent is caused to flow through the sealing assembly to transport particles from each rinsing chamber through a plurality of separate flow channels.

The present invention also provides a method for automatically calibrating one or more metering pumps. A workstation is provided and includes a fluid circulation system and a metering pump. A sampling module is provided and includes a sampling needle communicating with the fluid circulation system and a sample rack disposed on an open rack mounting region. A balance device is installed below the rack mounting region. The sample rack is removed from the rack mounting region. A reservoir is installed in the rack mounting region in operative engagement with the balance device. The metering pump is caused to transfer an indicated quantity of fluid through the fluid circulation system to the sampling needle, and the quantity of fluid is dispensed into the reservoir. The balance device is caused to measure an actual quantity of fluid dispensed into the reservoir. The metering pump is adjusted if the actual quantity measured by the balance device is different from the indicated quantity indicated by the metering pump.

It is therefore an object of the present invention to provide a workstation for automating steps required in the process of preparing solutions containing samples collected by a testing unit such as a particle impaction testing unit.

It is another object of the present invention to provide a workstation which establishes separate, sealed flow channels through various components of a particle testing unit.

It is a yet another object of the present invention to provide a workstation which includes an automated sealing assembly for various components of a particle testing unit.

It is a further object of the present invention to provide a workstation which includes custom fixtures adapted for mounting various components of a particle testing unit within a sealing assembly.

It is a still further object of the present invention to provide a workstation which includes a flow-through system for directing multiple solvents to and from various modules of the workstation with improved efficiency and under improved control, and which is operable between open and closed loops.

It is an additional object of the present invention to provide a workstation which includes a sampling module which enables parallel transfer of solvent to several and different types of solvent vial racks and vials without the need for reconfiguration or adjustment of the sampling module or sampling needles and solvent transfer lines associated with the sampling module.

It is also an object of the present invention to provide an automated system for calibrating metering pumps included with a rinsing and sample collection workstation.

Testing and validation conducted by applicants has demonstrated that the workstation provided according the present invention and its associated systems and assemblies are capable of yielding data equivalent to that typically observed in conjunction with conventional manual testing.

Some of the objects of the invention having been stated hereinabove, other objects will become evident as the description proceeds when taken in connection with the accompanying drawings as best described hereinbelow.

BRIEF DESCRIPTION OF THE DRAWINGS

FIG. 16 is a perspective view of a throat fixture and associated throat according to the present invention;

DETAILED DESCRIPTION OF THE INVENTION

Figure 1:
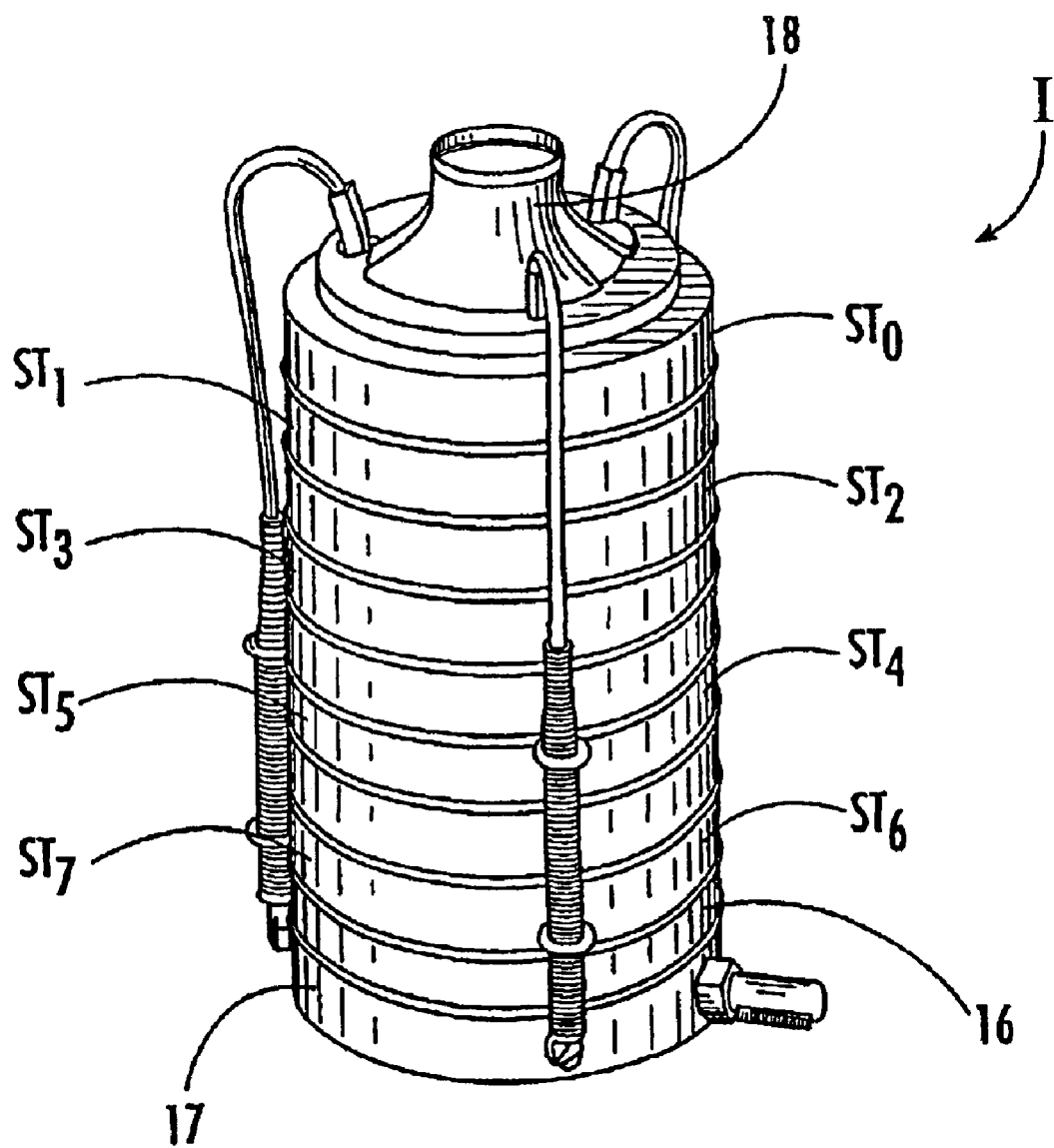
FIG. 1 is a front elevation view of a cascade impactor unit known in the prior art and usable in conjunction with the present invention.
Figure 2:
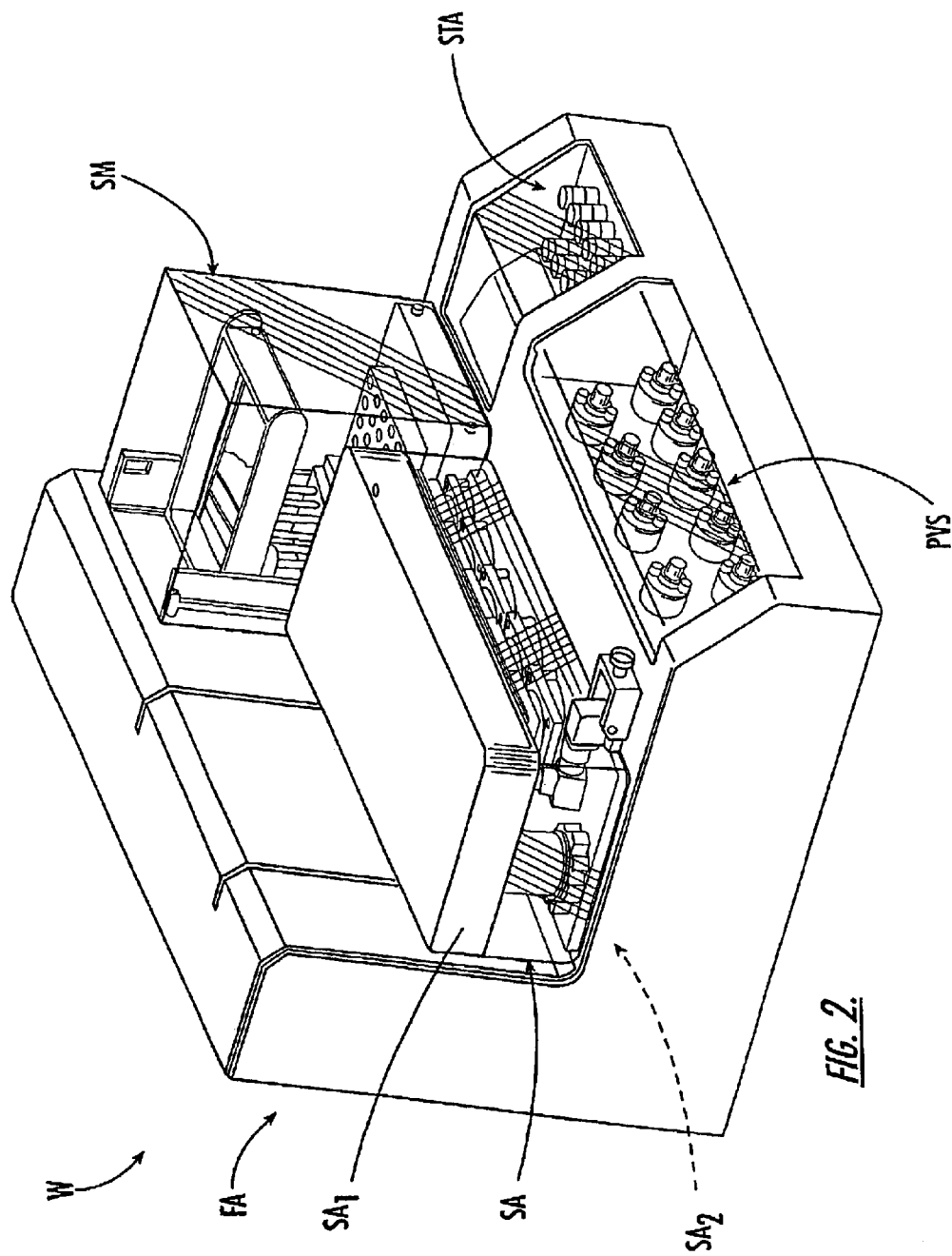
FIG. 2 is a perspective view of an automated rinsing and sample collection workstation according to the present invention.

Referring to FIGS. 2–9, an automated rinsing and sample collection workstation generally designated W is provided in accordance with the present invention. Referring particularly to FIG. 2, workstation W includes a frame assembly generally designated FA on which several modules are mounted. The modules include an automated sealing assembly generally designated SA and an automated solvent flow-through system, which flow-through system is defined by an automated metering pump and valve system generally designated PVS, a solvent tube arrangement generally designated STA and an automated sampling module generally designated SM. The operation of the solvent flow-through system and the interaction of its various components is described hereinbelow. All automated modules can be programmed and controlled by software.

Figure 3:
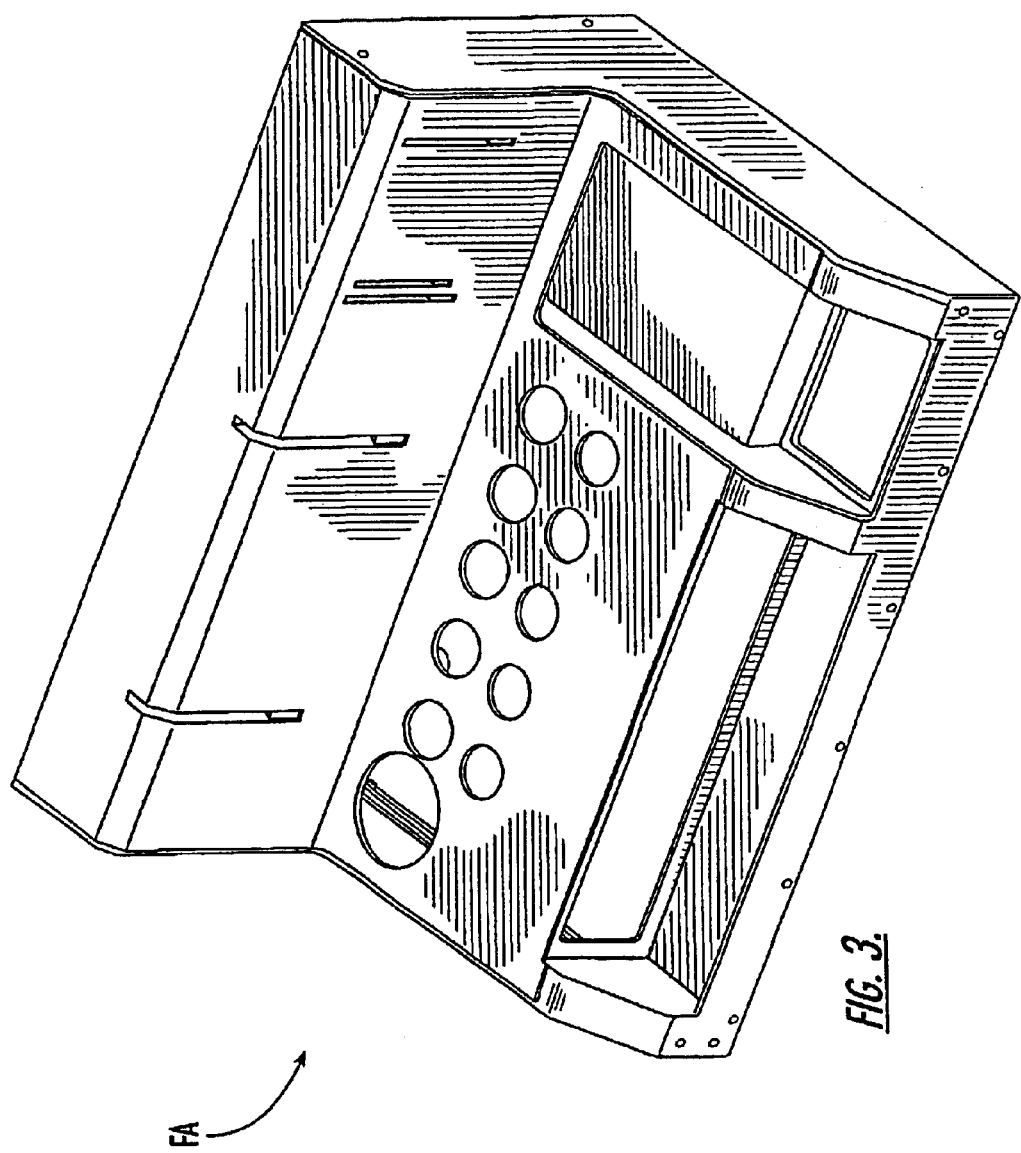
FIG. 3 is a perspective view of the framework provided for the workstation of FIG. 2.
Figure 4:
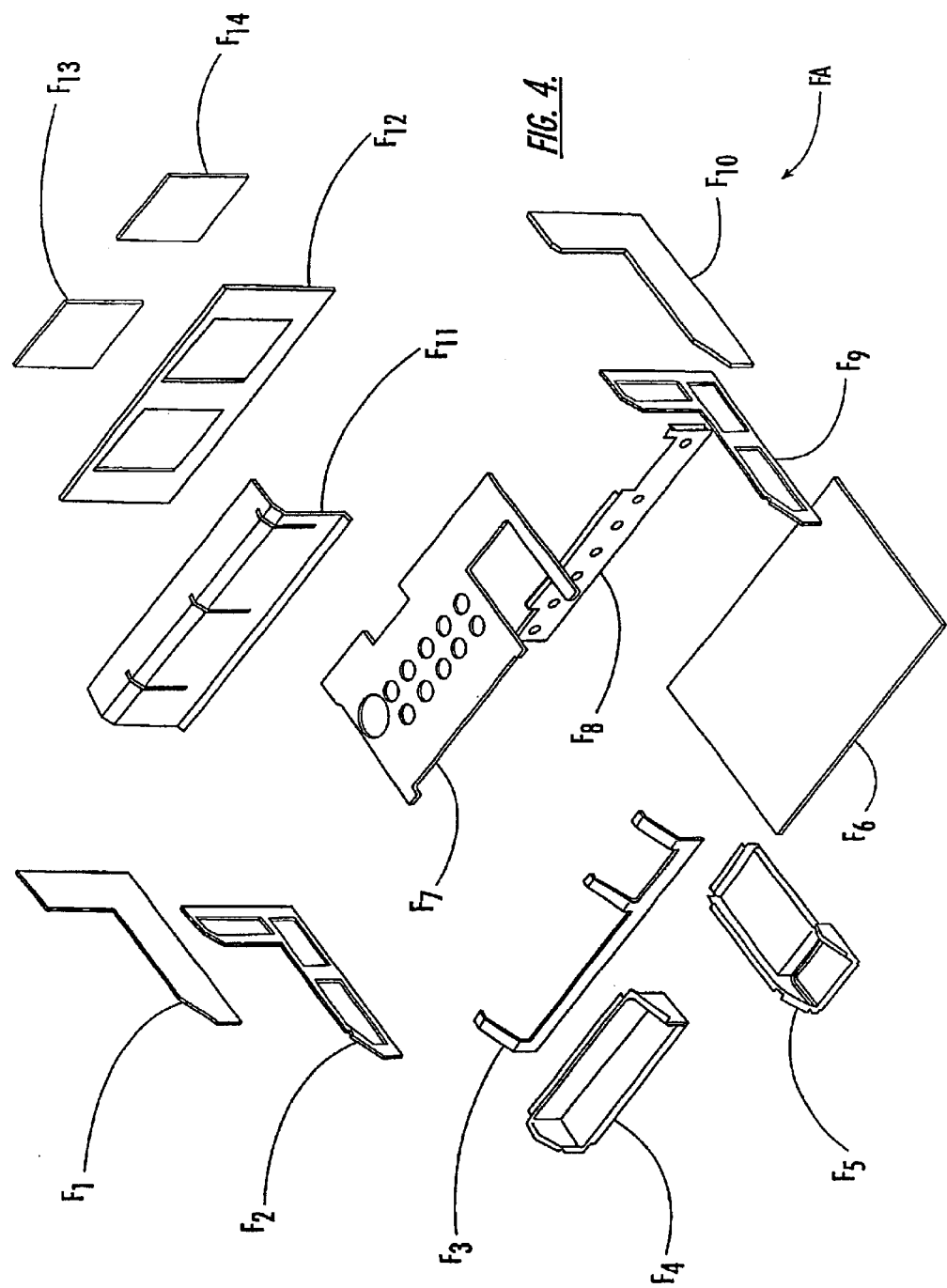
FIG. 4 is an exploded view of the framework of FIG. 3.

FIGS. 3 and 4 illustrate frame assembly FA in assembled and exploded forms, respectively. As shown in FIG. 4, frame assembly FA is constructed from several frame elements $F_1$–$F_{14}$.

Figure 5:
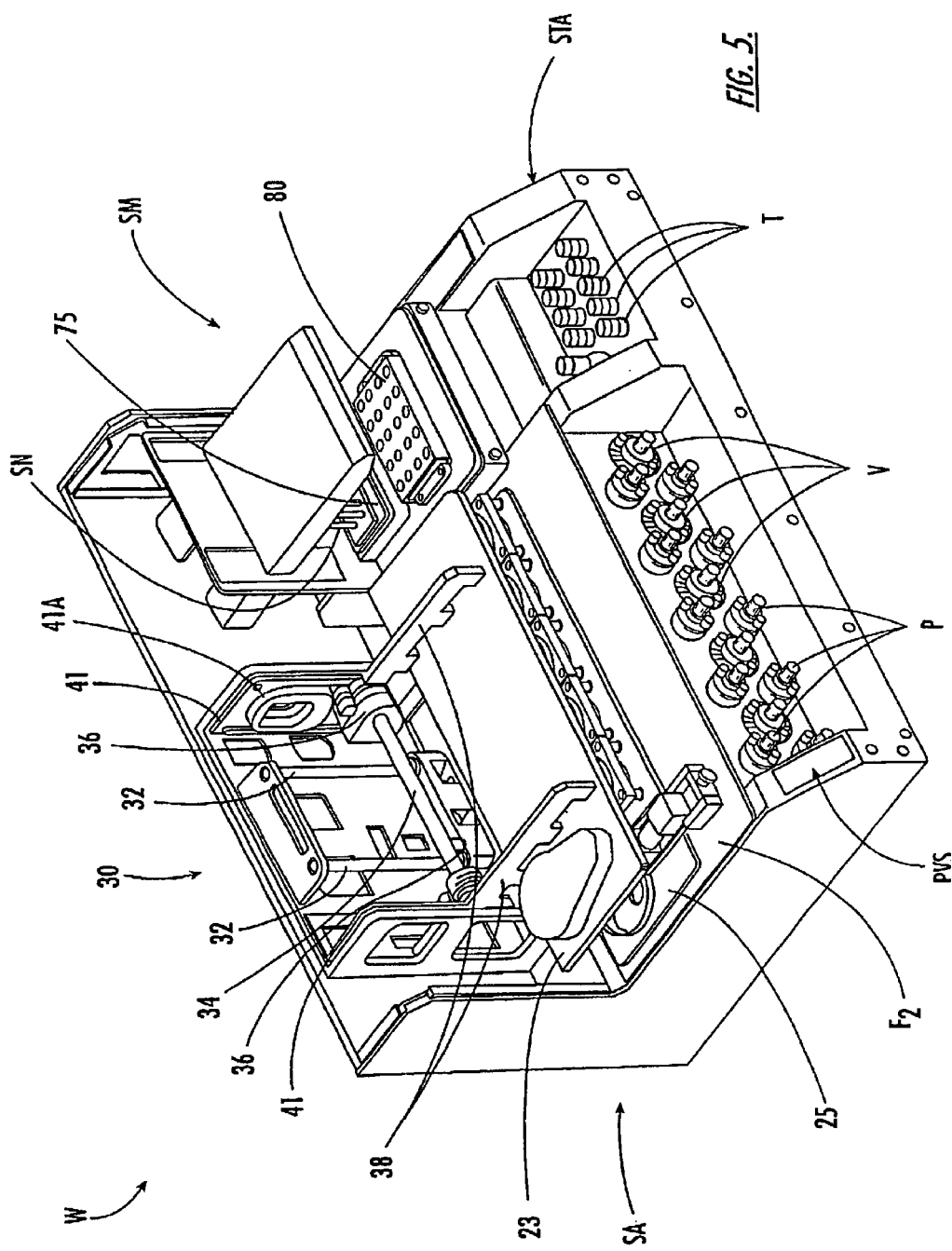
FIG. 5 is a perspective view of the workstation of FIG. 2 with a portion of the framework removed.
Figure 33:
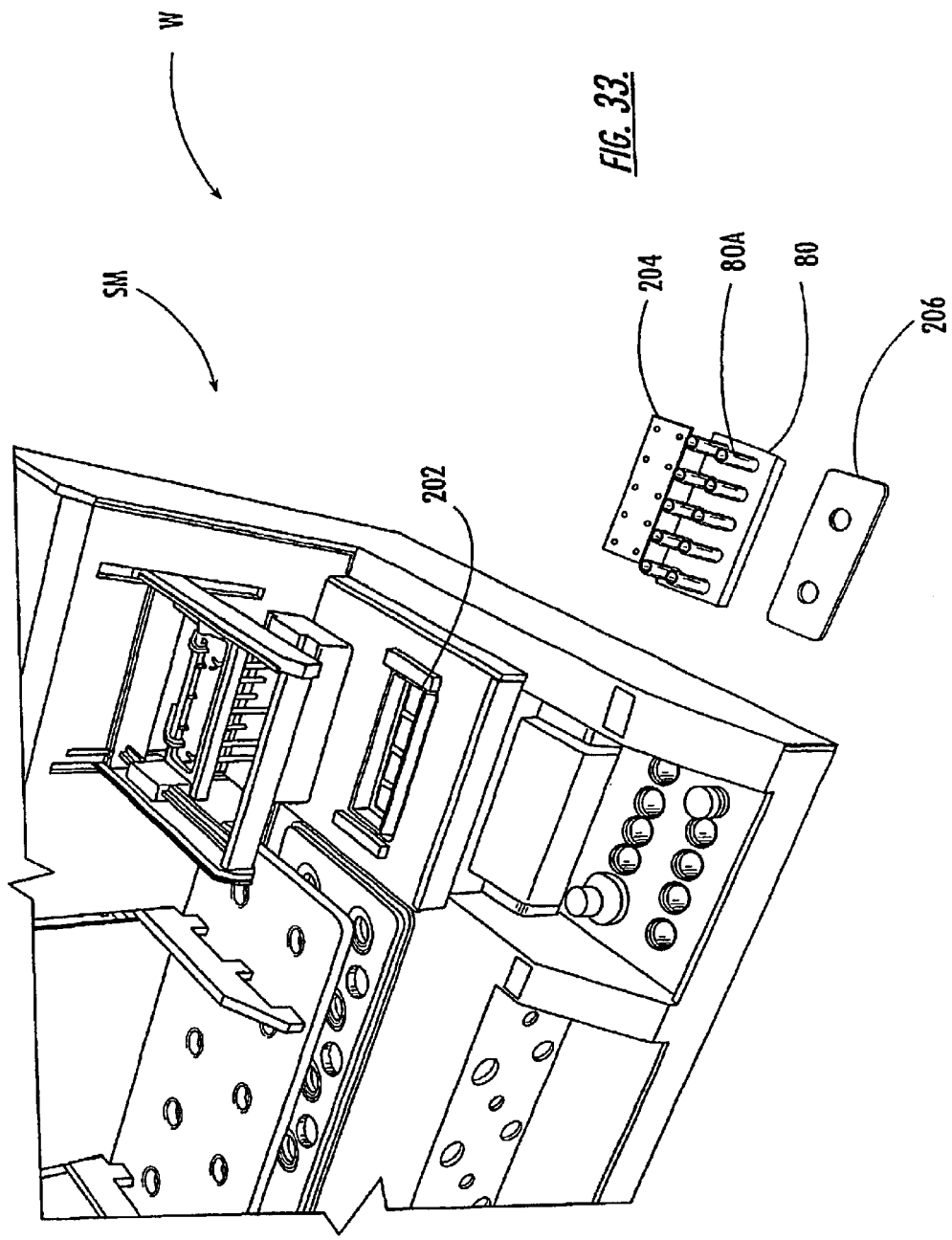
Figure 34:
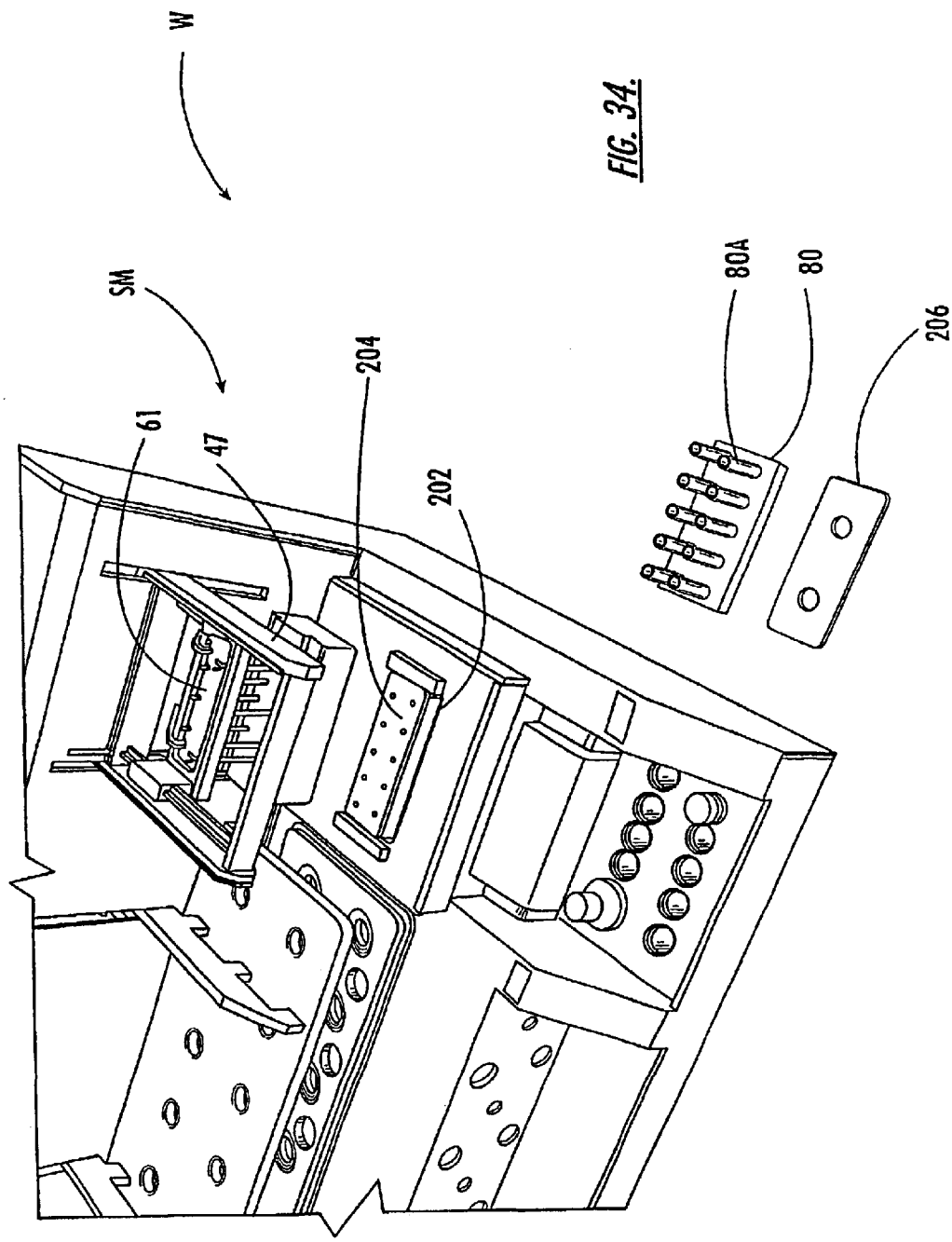
Figure 35:
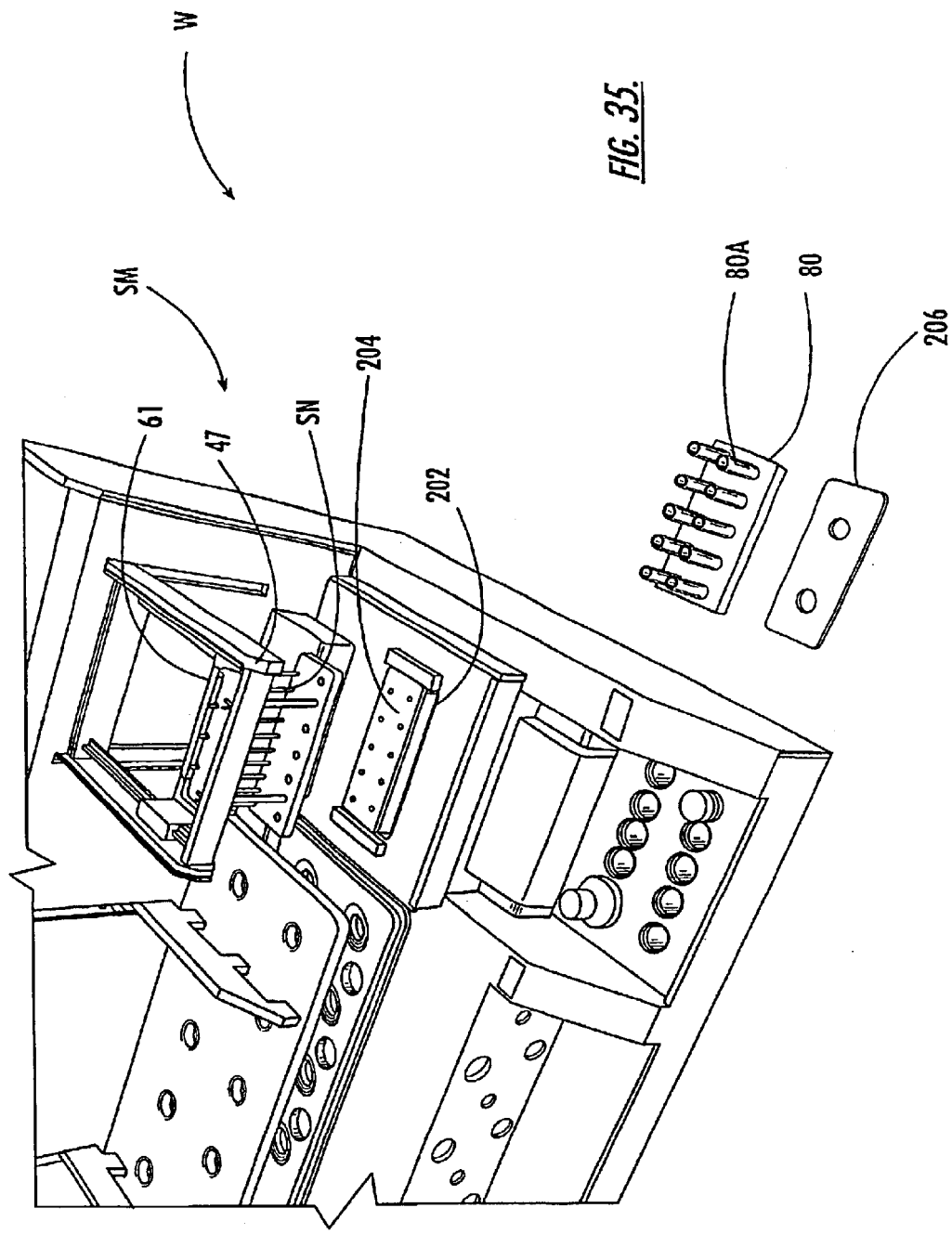

Referring to FIG. 5, sealing assembly SA includes an upper clamping plate 23, a lower clamping plate 25, and a clamping drive subassembly generally designated 30. Clamping drive subassembly 30 includes two lead screws 32 driven by a linear axis motor, an axle 34 supported by axle support members 36, and support brackets 38 guided by tracks 41A of track plates 41. Upper clamping plate 23 is attached to support brackets 38, while lower clamping plate 25 is mounted to deck or frame member $F_7$. Clamping drive subassembly 30 operates to drive upper clamping plate 23 from an open position as shown in FIG. 33, through intermediate positions as shown in FIG. 34, and ultimately to a closed, sealed position as shown in FIG. 35. Sealing assembly SA thus can be characterized as having a clamshell-type configuration.

Figure 6:
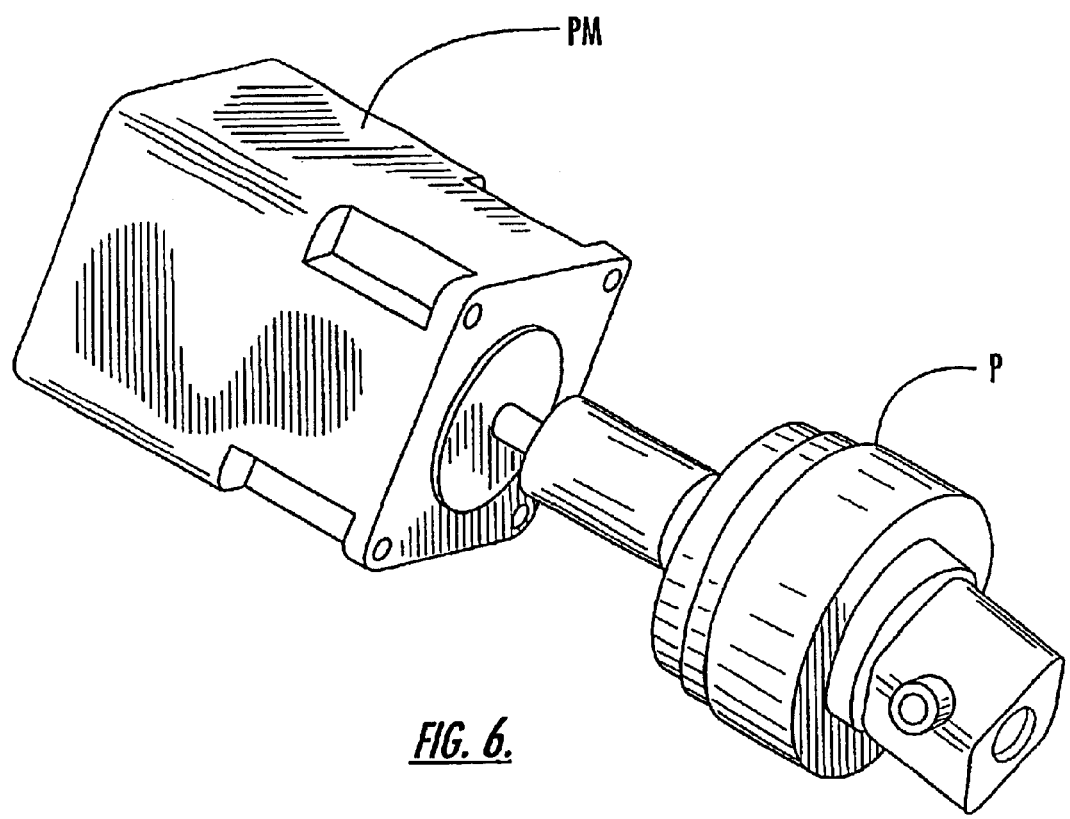
FIG. 6 is a perspective view of a metering pump and associated drive according to the present invention.

Metering pump and valve system PVS includes a plurality of pumps P and valves V. Pumps P can be considered in pairs, wherein each pair of pumps P shares a single multi-position valve V. Multi-position valves V permit the introduction of multiple solvents at different phases of drug recovery and system cleanup. In the present exemplary embodiment, there are ten pumps P for establishing ten separate flow channels and hence five valves V. Each flow channel is characterized by its own separate pump and valve subsystem. As shown in FIG. 6, each pump P is driven by a pump drive preferably in the form of a servo motor PM.

Solvent tube arrangement STA is part of the fluid circuit of the solvent flow-through system. In the present embodiment, there are ten solvent tubes T corresponding to the ten flow channels.

Figure 7:
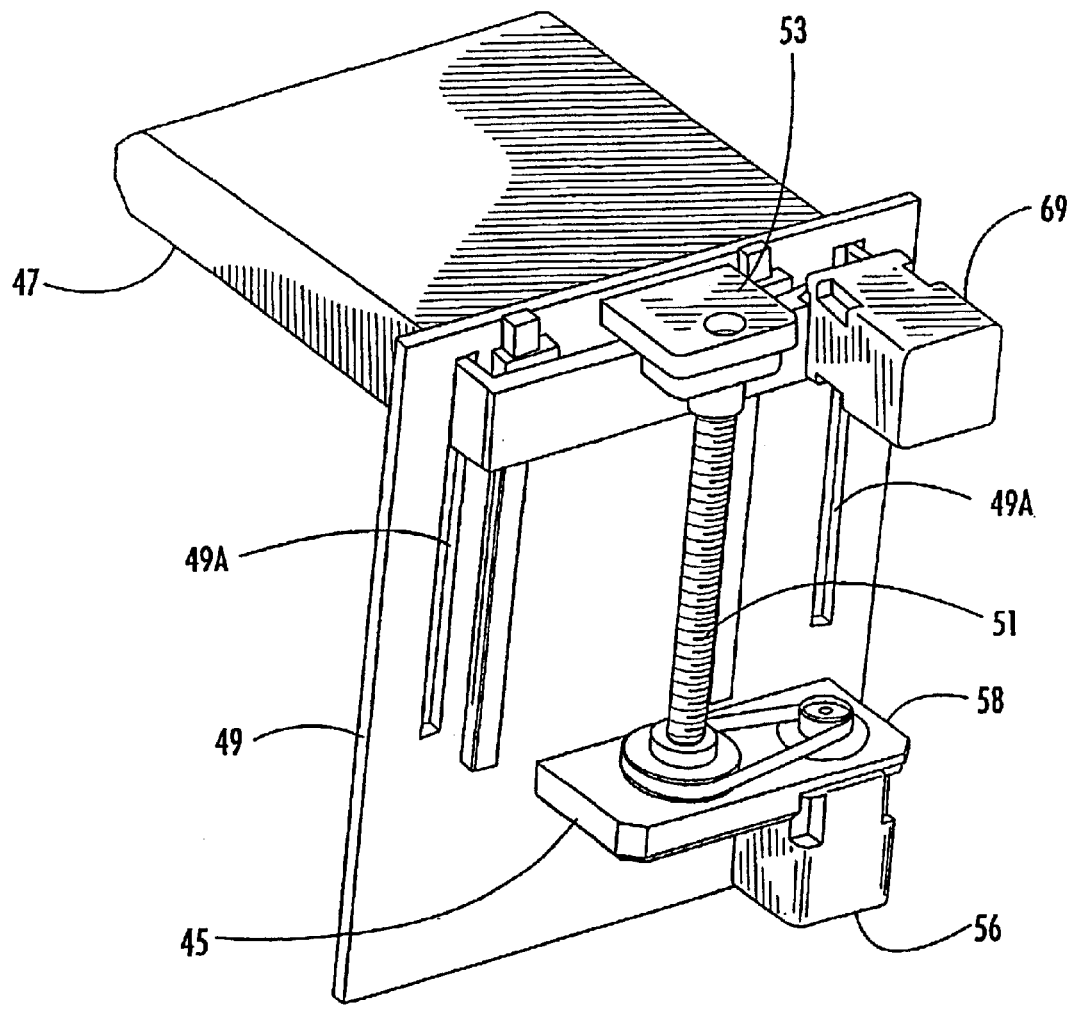
FIG. 7 is a perspective view of a sampling module according to the present invention.
Figure 8:
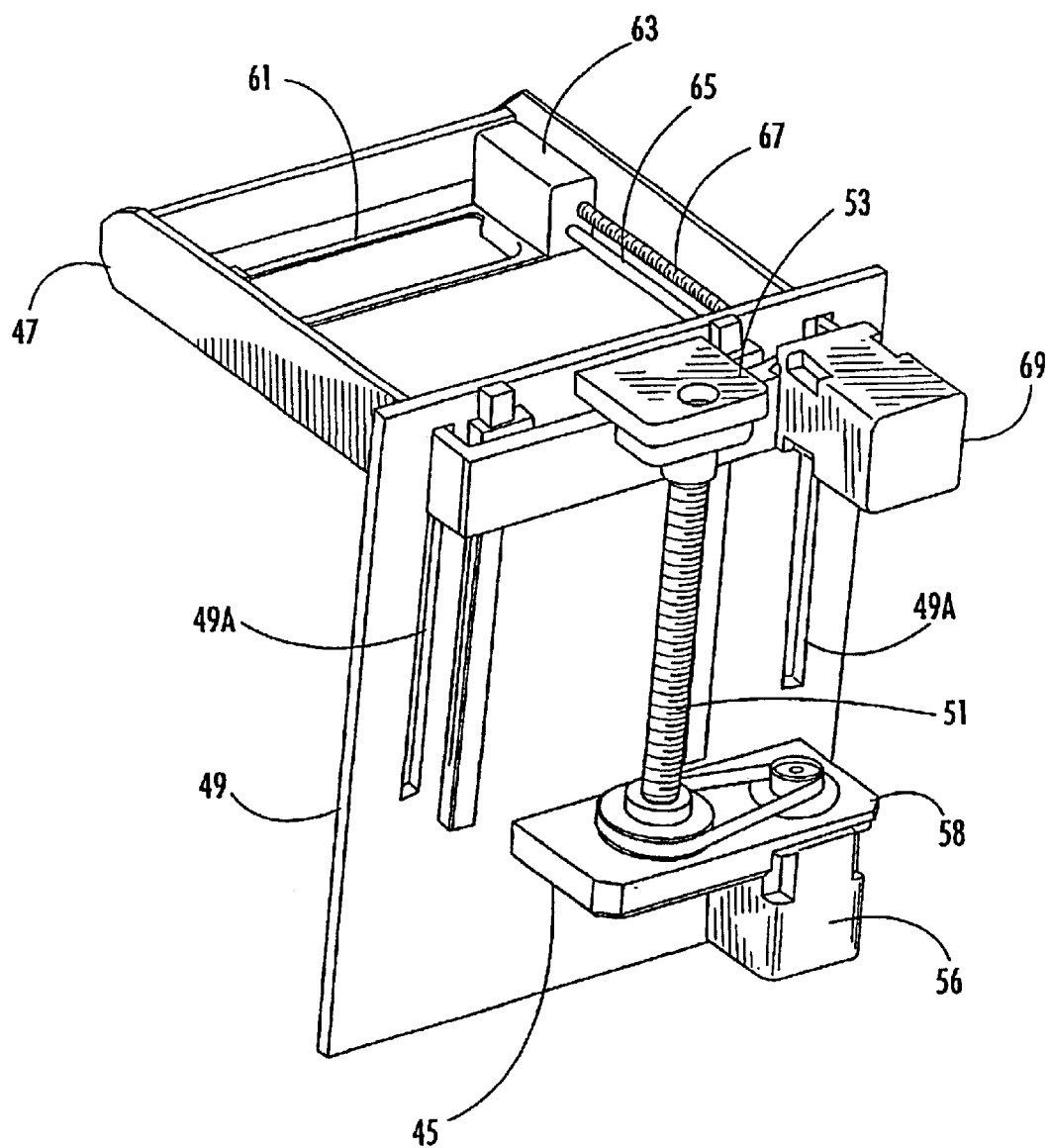
FIG. 8 is a perspective view of the sampling module of FIG. 7 with a cover thereof removed.

Referring to FIGS. 7 and 8, sampling module SM is actuated by a sampling module drive assembly generally designated 45. Sampling module drive assembly 45 includes a vertically movable first bracket 47 guided in tracks 49A of a back plate 49. First bracket 47 is driven by a lead screw 51 through a movable drive head 53. Lead screw 51 is powered by a linear axis motor 56 through a drive transmission 58. A horizontally movable second bracket 61 is supported by a movable drive head 63 and is guided along two guide rods 65 (only one of which is shown) and lead screw 67, both of which are mounted to first bracket 47. Also mounted to first bracket 47 and movable therewith is a linear axis motor 69 providing torque power to lead screw 67. Referring back to FIG. 5, sampling module SM includes an array (e.g., ten) sampling needles SN movable by second bracket 61, a waste receptacle 75, and a test tube or vial rack 80. Sampling module SM operates to transfer samples collected by sealing assembly SA to test tubes or vials positioned on rack 80, as described in more detail hereinbelow.

Figure 9:
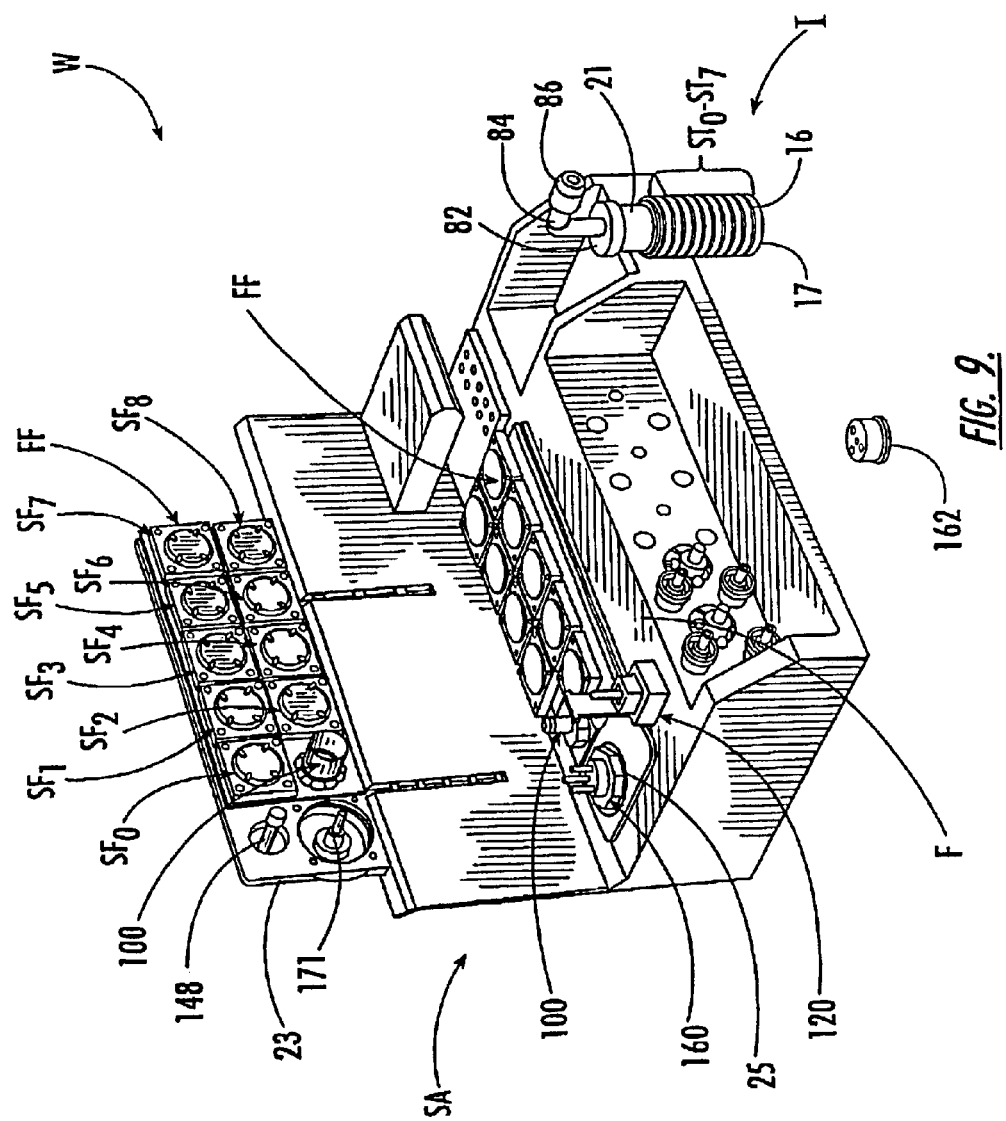
FIG. 9 is a perspective view of the workstation of FIG. 2 illustrating fixtures provided therewith.

Referring generally to FIG. 9, workstation W is shown with a multistage impactor such as cascade impactor I. Impactor I includes stage zero $ST_0$, classification stages $ST_1$–$ST_7$, bottom filter 16, base element 17, pre-separator 21, a cover 82, a throat 84, and a mouthpiece 86 serving as an interface between impactor I and the actuator used to dose impactor I. Workstation W includes a number of fixtures provided for mounting and sealing the various elements of impactor I within sealing assembly SA. These fixtures include a stage fixture generally designated $SF_0$ for stage zero $ST_0$, stage fixtures generally designated $SF_1$–$SF_7$ for stages $ST_1$–$ST_7$, a filter fixture generally designated FF for filter 16, a mouthpiece fixture generally designated 100, a throat fixture generally designated 120, and a pre-separator fixture generally designated 160 or inlet cone fixture generally designated 180. Portions of each fixture $SF_0$–$SF_7$, FF, 100, 120, and 160 or 180 are mounted to both upper and lower clamping plates 23 and 25.

Figure 10:
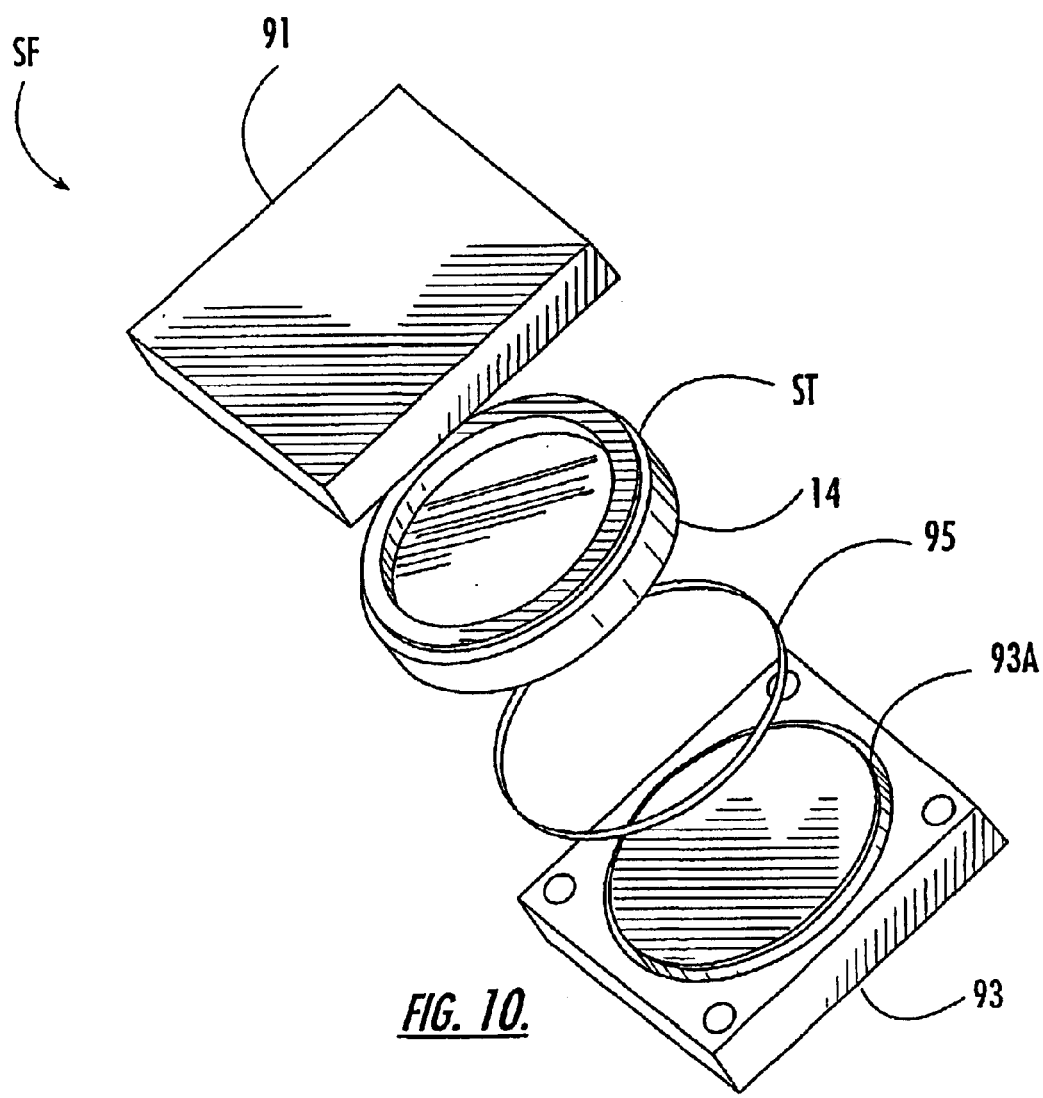
FIG. 10 is an exploded view of a stage fixture and associated stage according to the present invention.
Figure 11:
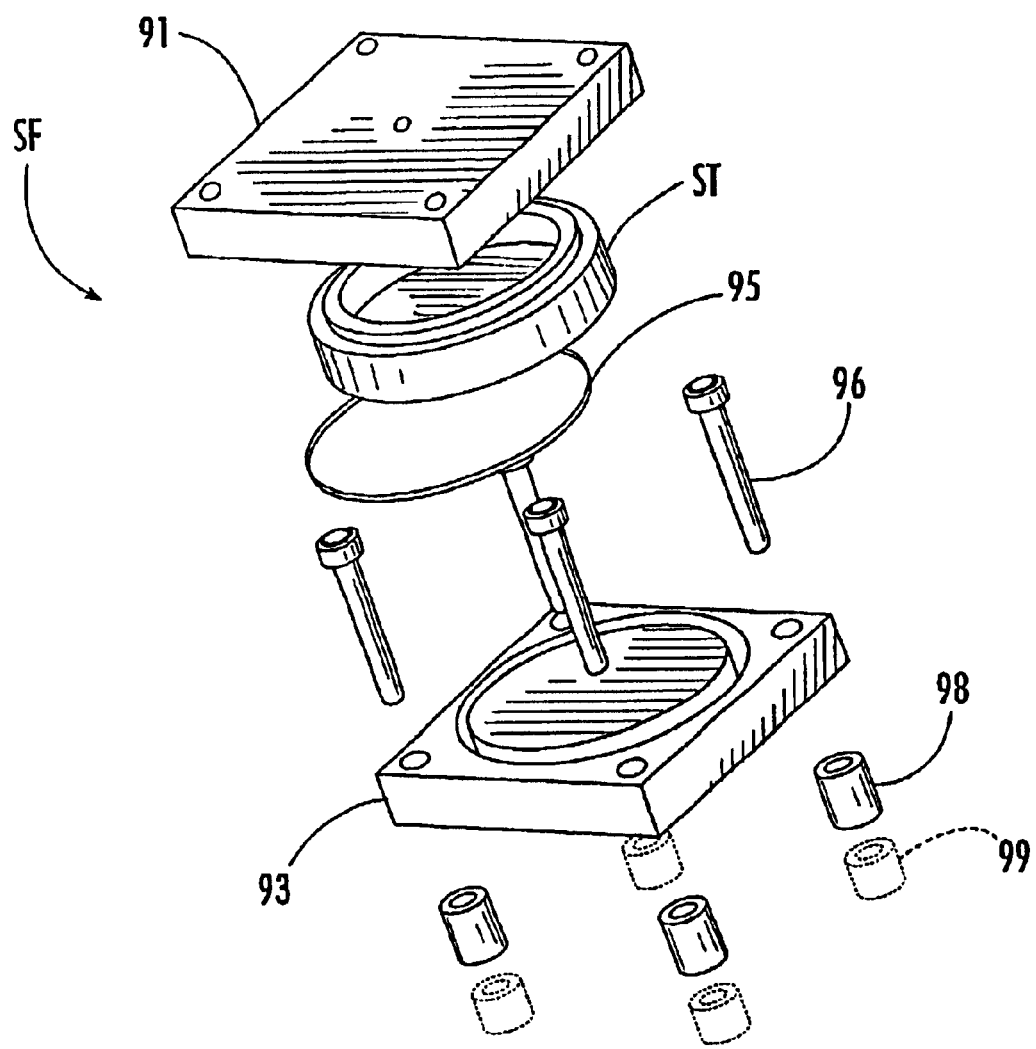
FIG. 11 is another exploded view of a stage fixture and associated stage of FIG. 10.
Figure 12:
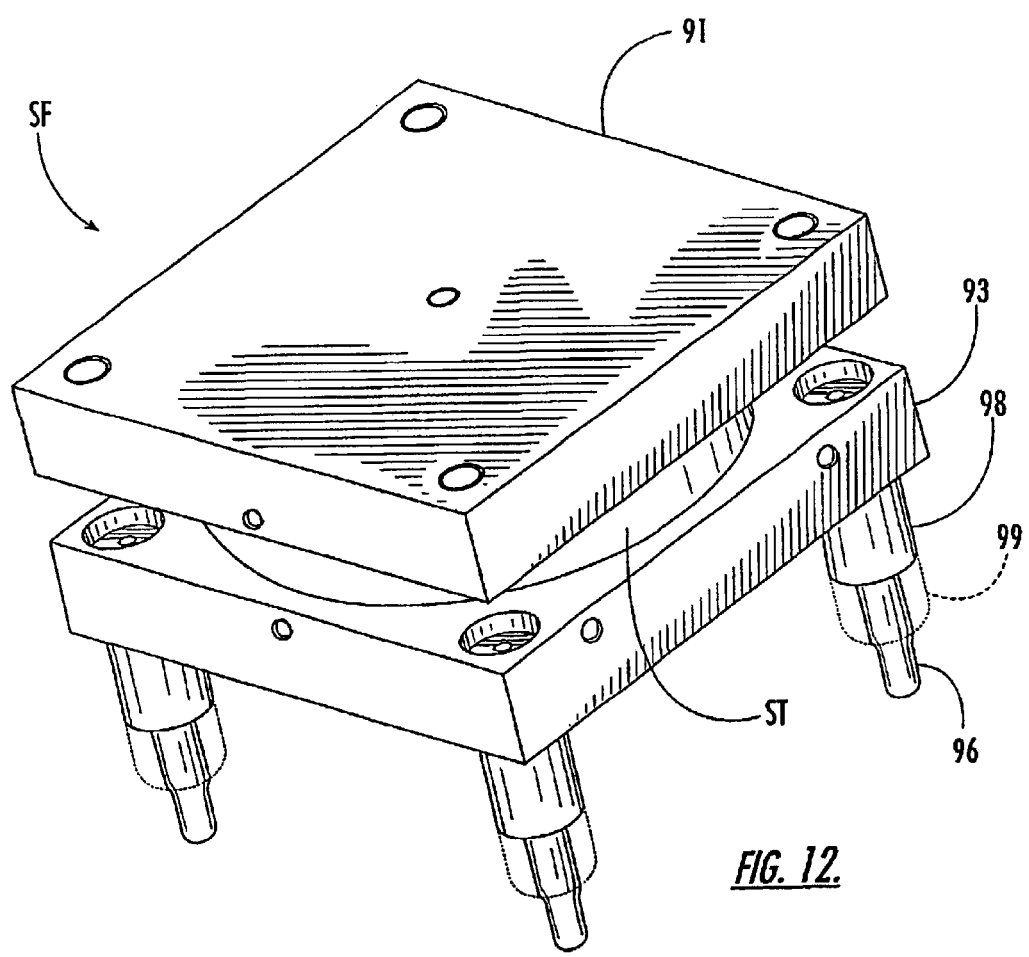
FIG. 12 is a perspective view of the stage fixture and associated stage illustrated in sealed form.

Referring to FIGS. 10–12, each stage fixture $SF_0$–$SF_7$ and filter fixture FF includes an upper stage adaptor 91 mounted to upper clamping plate 23 and a lower stage adaptor 93 mounted to lower clamping plate 25 using fastening elements 96, spacers 98 and springs 99. Each stage ST or filter 16 is sealed between upper and lower stage adaptors 91 and 93 corresponding to that particular stage ST or filter 16. Lower stage adaptor 93 has a circular groove 93A for receiving a ring seal 95 between stage ST and lower stage adaptor 93.

Figure 13:
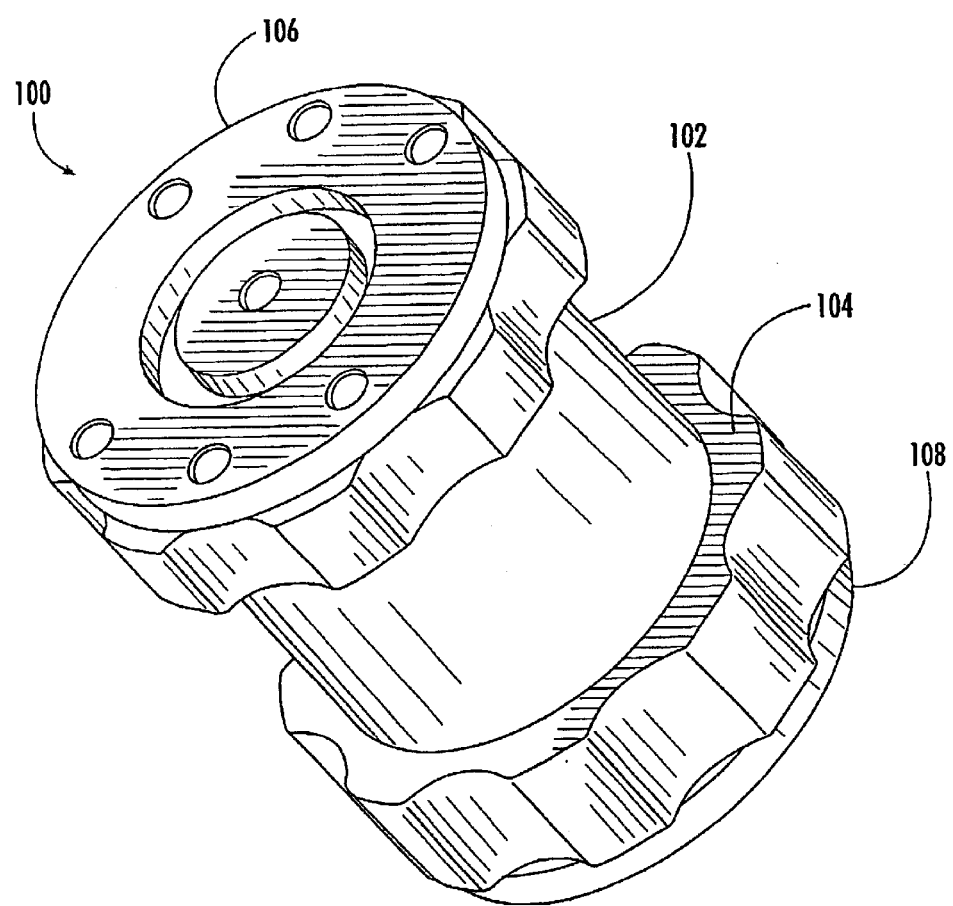
FIG. 13 is a perspective view of a mouthpiece fixture illustrated in sealed form.
Figure 14:
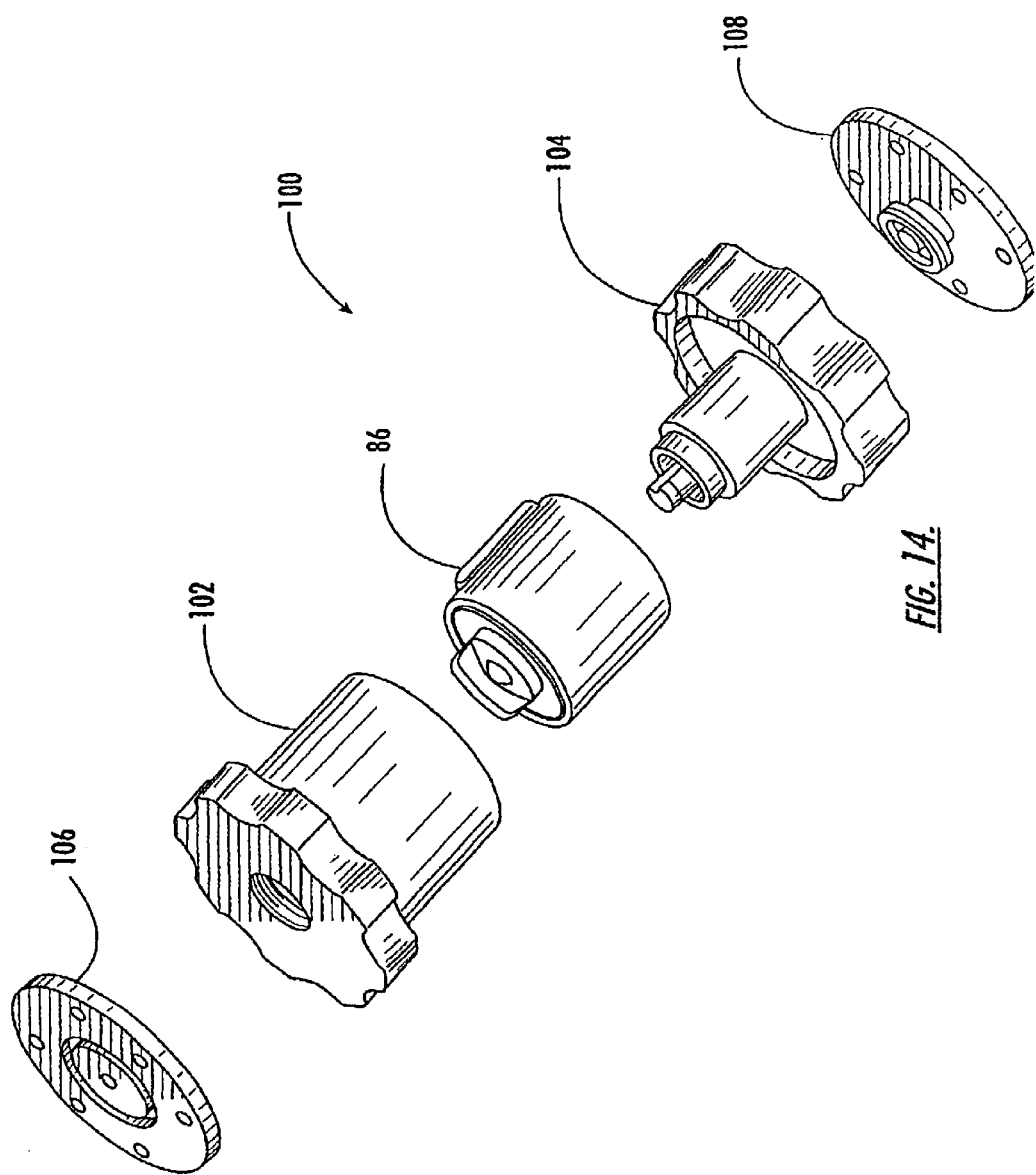
FIG. 14 is an exploded view of the mouthpiece fixture of FIG. 13 with an associated mouthpiece.
Figure 15:
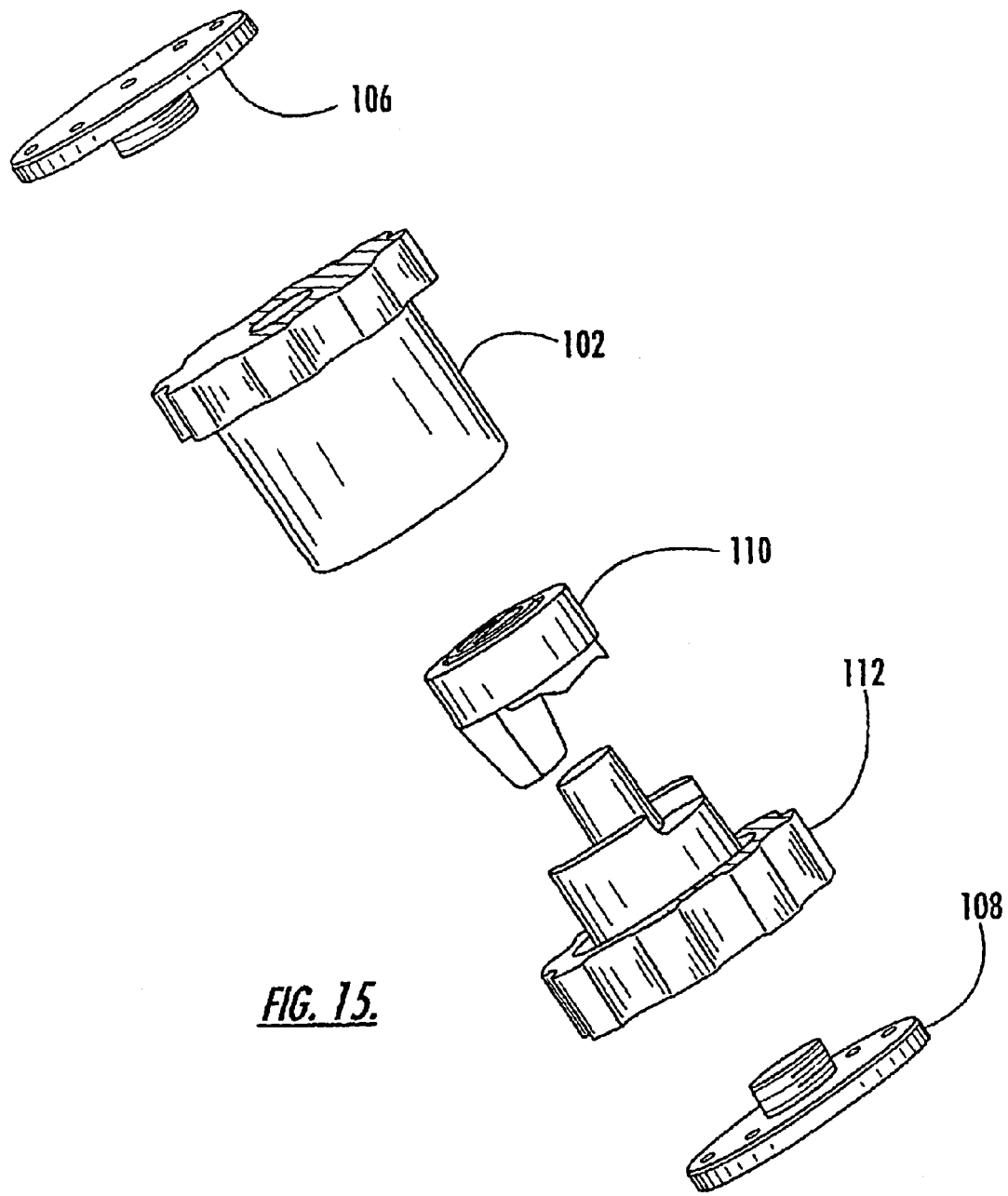
FIG. 15 is an exploded view of another mouthpiece fixture with another associated mouthpiece.

Referring to FIGS. 13 and 14, mouthpiece fixture 100 includes an upper mouthpiece adaptor 102 and a lower mouthpiece adaptor 104. Mouthpiece 86 is sealed between upper and lower mouthpiece adaptors 102 and 104. Upper mouthpiece adaptor 102 is mounted to an upper mounting plate 106 which is in turn mounted to upper clamping plate 23. Lower mouthpiece adaptor 104 is mounted to a lower mounting plate 108 which is in turn mounted to lower clamping plate 25. FIG. 15 illustrates an alternative mouthpiece 110 and a corresponding lower mouthpiece adaptor 112.

Figure 17:
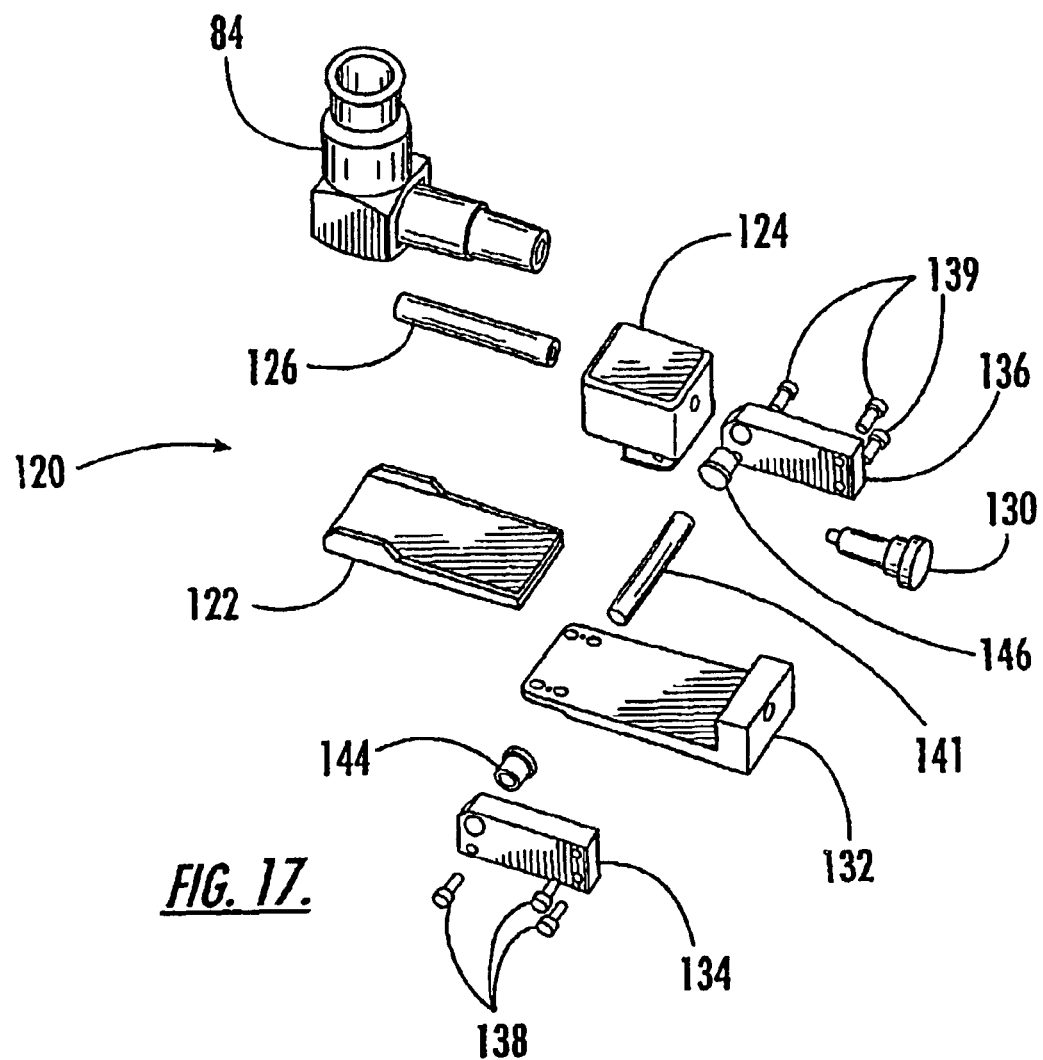
FIG. 17 is an exploded view of the throat fixture and associated throat of FIG. 16.
Figure 18:
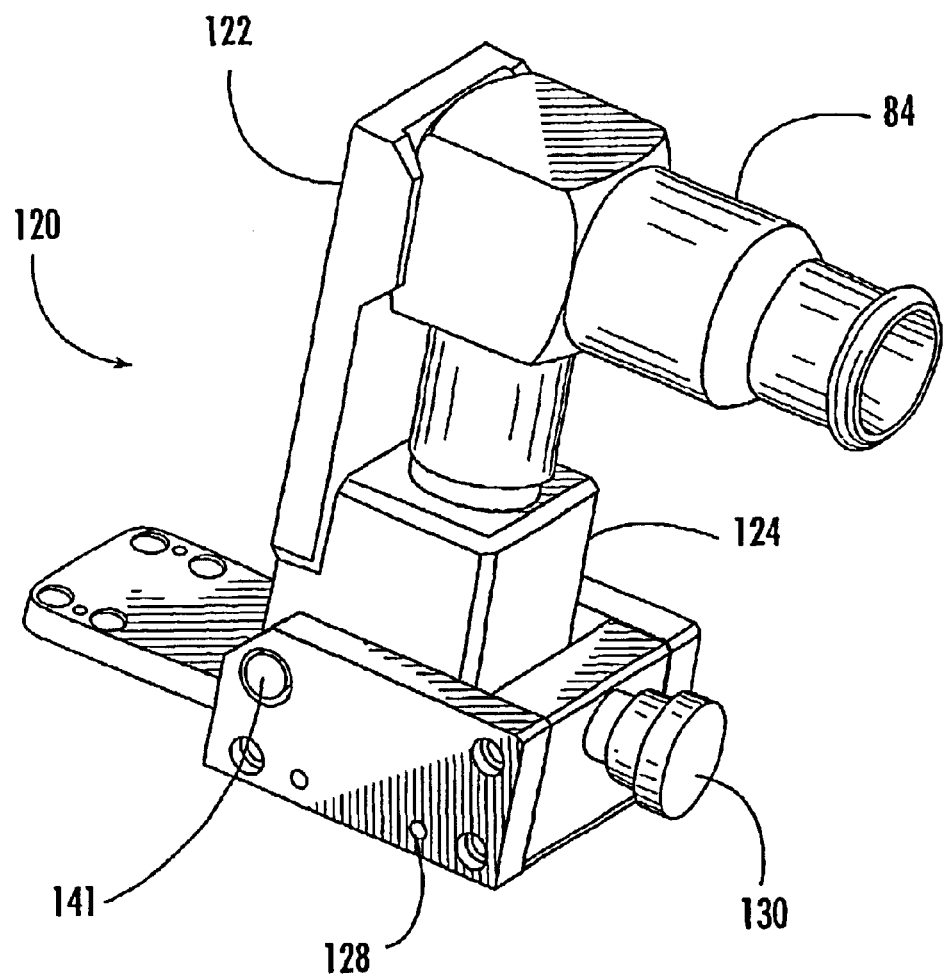
FIGS. 18, 19, 20 and 21 are perspective views of the throat fixture of FIG. 16 with the throat loaded therein.
Figure 19:
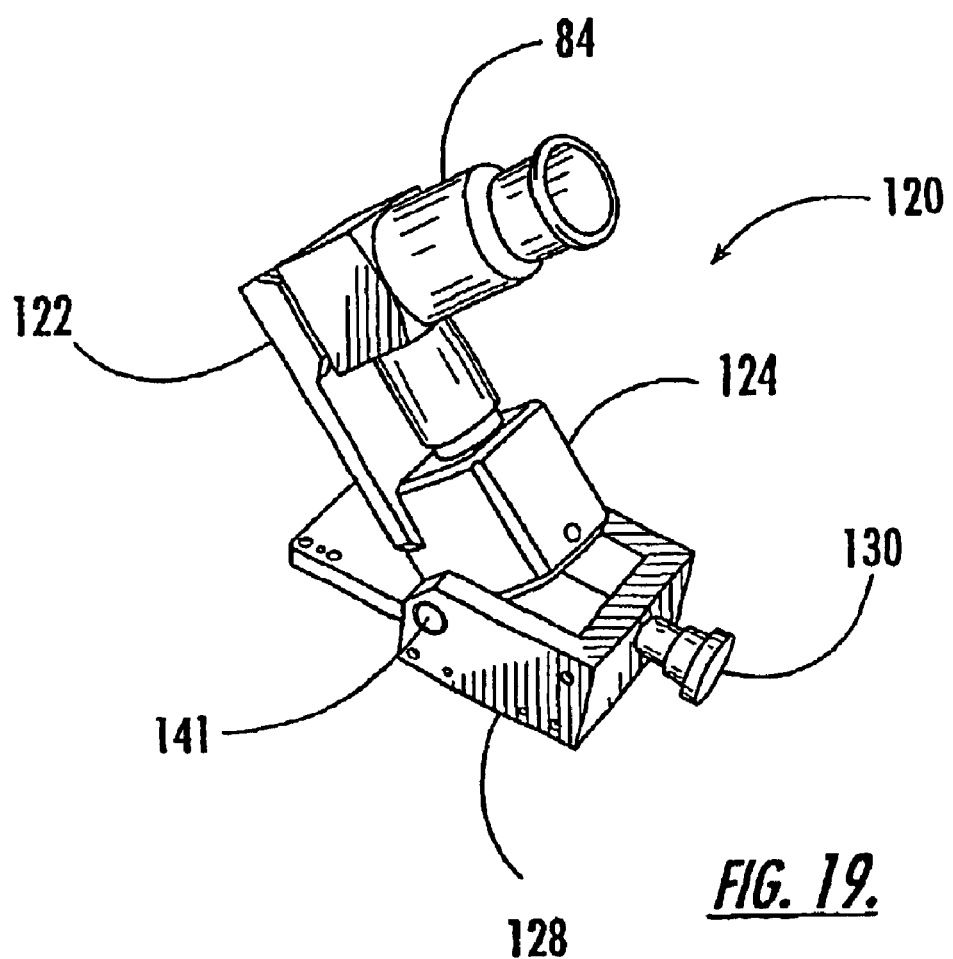
Figure 20:
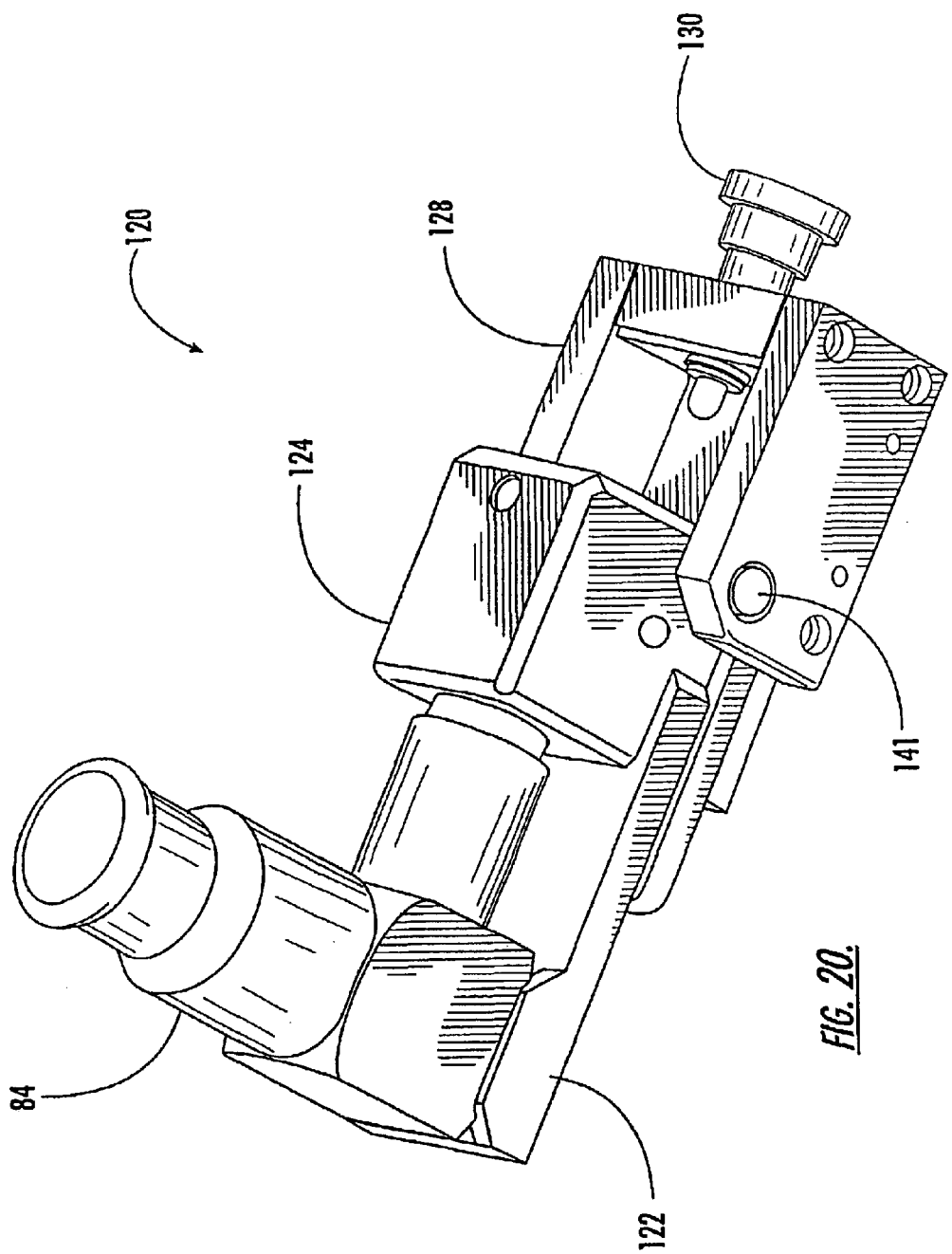
Figure 21:
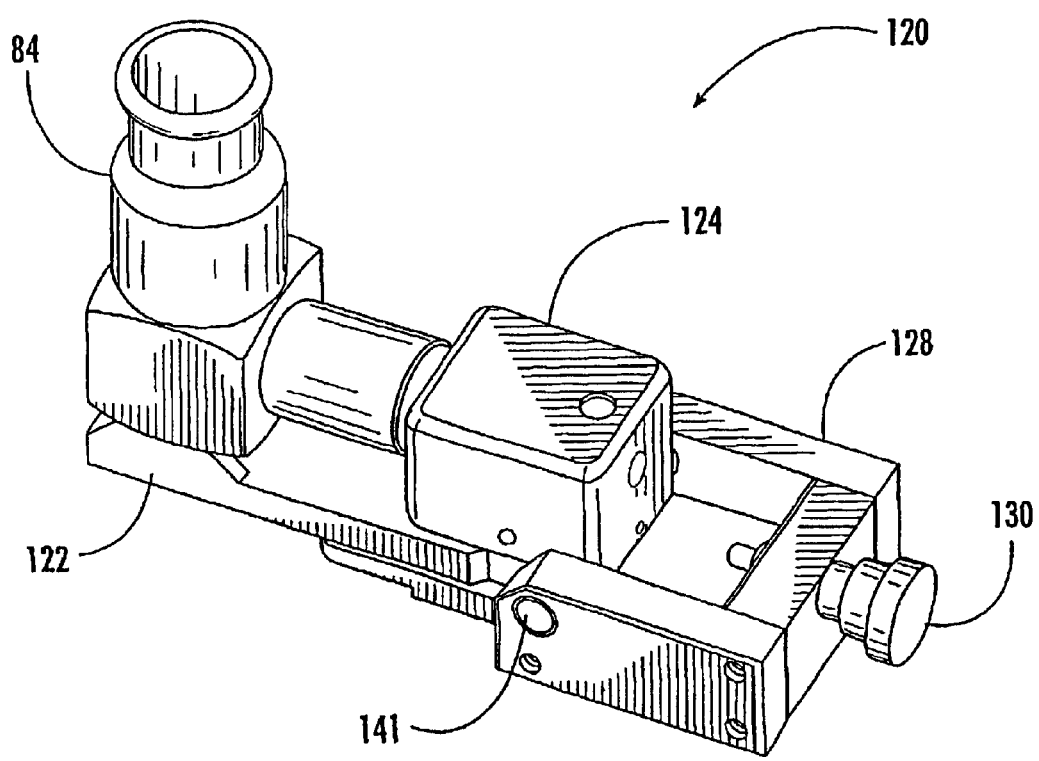

Referring to FIGS. 16 and 17, throat fixture 120 includes an upper throat adaptor 122, a lower throat adaptor 124, a mounting post 126, a mounting block 128, and a locking mechanism 130. Mounting block 128 includes an L-shaped base plate 132 and two side plates 134 and 136 secured thereto with fasteners 138 and 139. Mounting block 128 is mounted to deck or frame element $F_7$ in front of lower clamping plate 25. An axle 141 is secured to side plates 134 and 136 in bearings 144 and 146. Lower throat adaptor 124 is provided in the form of a socket and is adapted for receiving mounting post 126. Axle 141 extends through lower throat adaptor 124 such that lower throat adaptor 124 can rotate about axle 141 once locking mechanism 130 is disengaged from lower throat adaptor 124. Upper throat adaptor 122 is provided in the form of a plate and is secured between lower throat adaptor 124 and L-shaped base plate 132. As shown in FIGS. 18–21, a first end 84A of throat 84 is positioned onto mounting post 126 and rotates with upper and lower throat adaptors 122 and 124 from a vertical position to a horizontal position upon release of locking mechanism 130. As shown in FIG. 9, throat fixture 120 also includes an elongate throat sealing member 148 mounted to upper clamping plate 23. Throat sealing member 148 inserts into a second end 84B of throat 84 when upper clamping plate 23 is closed onto lower clamping plate 25.

Figure 22:
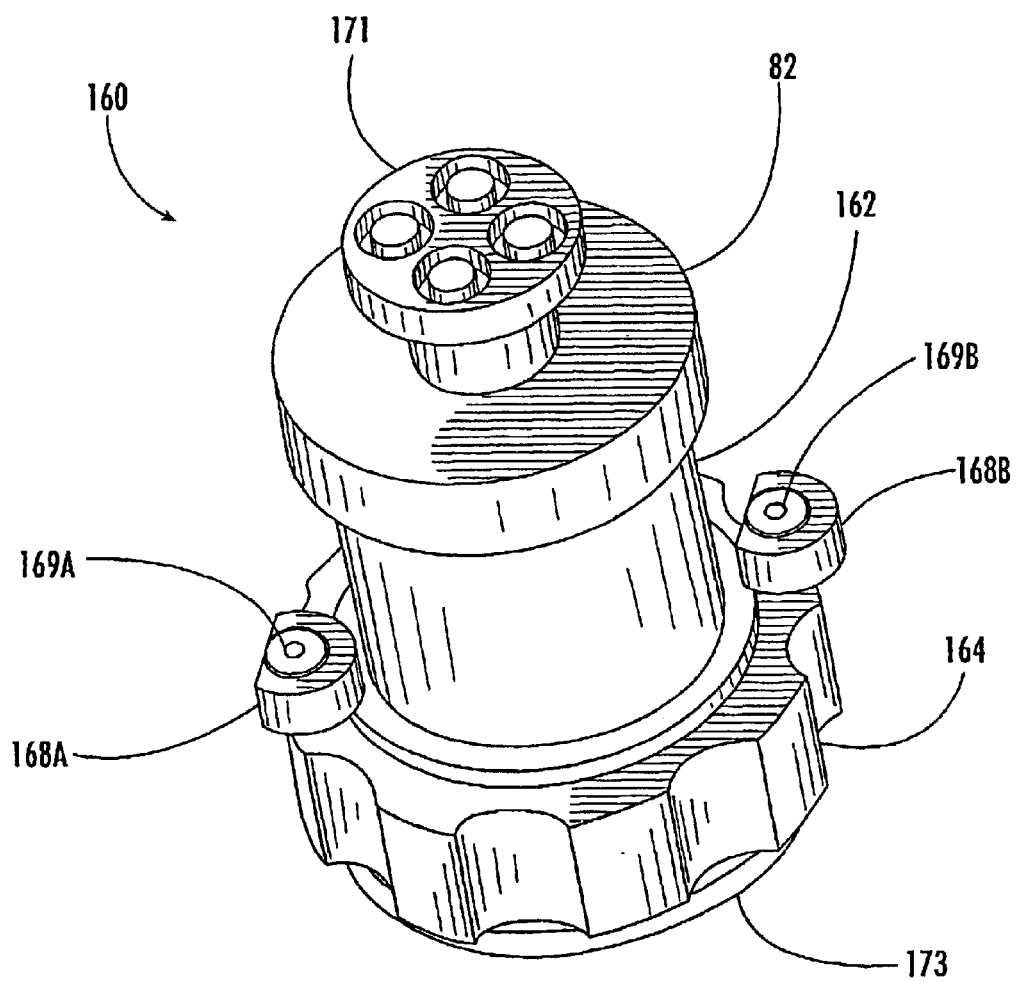
FIG. 22 is a perspective view of a pre-separator fixture according to the present invention.
Figure 23:
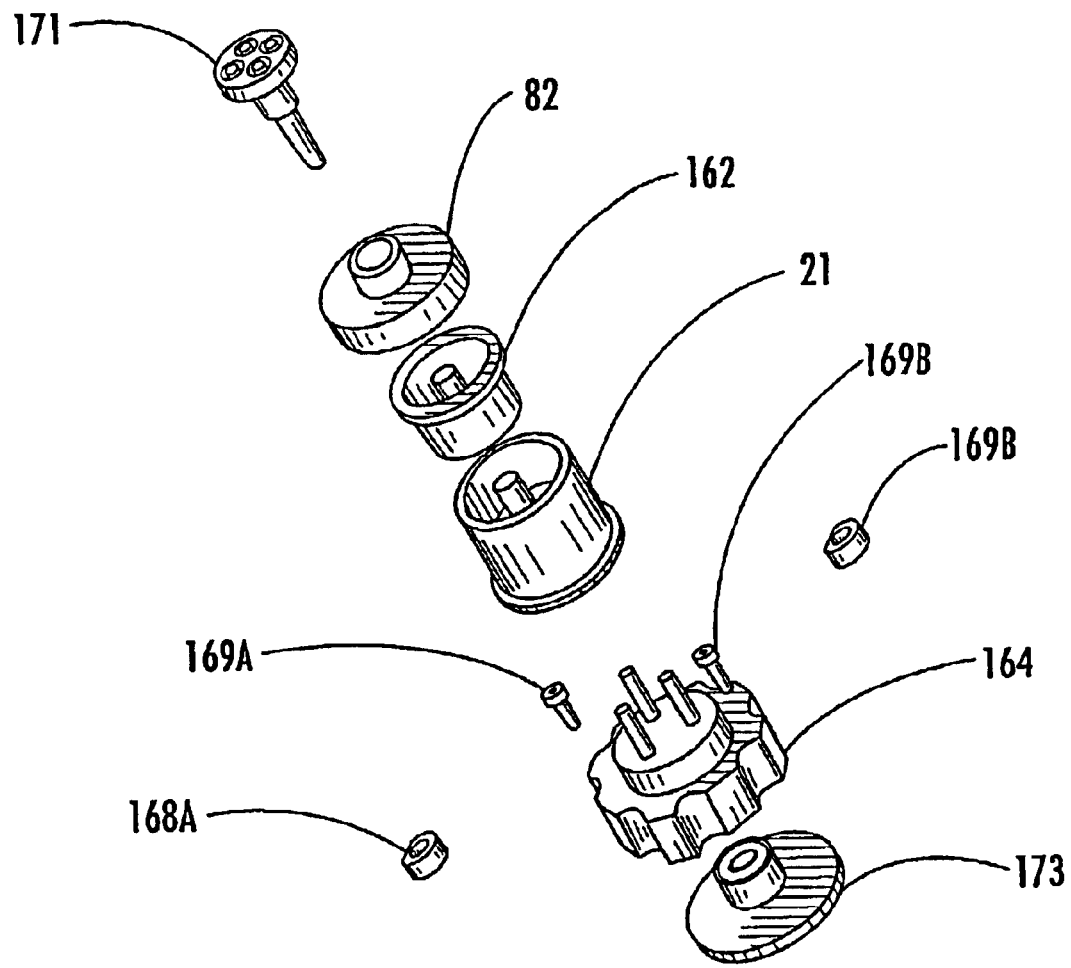
FIG. 23 is an exploded view of the pre-separator fixture of FIG. 22 with an associated pre-separator.

Referring to FIGS. 22 and 23, pre-separator fixture 160 includes an upper pre-separator adaptor 162 and a lower pre-separator adaptor 164. Pre-separator 21 is sealed between upper and lower pre-separator adaptors 162 and 164 with the assistance of locking mechanisms 168A and 168B secured to lower pre-separator adaptor 164 with fasteners 169A and 169B. Cover 82 from impactor I and upper pre-separator adaptor 162 are mounted to a mounting post 171, which is in turn mounted to upper clamping plate 23. Lower pre-separator adaptor 164 is mounted to a mounting plate 173, which is in turn mounted to lower clamping plate 25.

Figure 24:
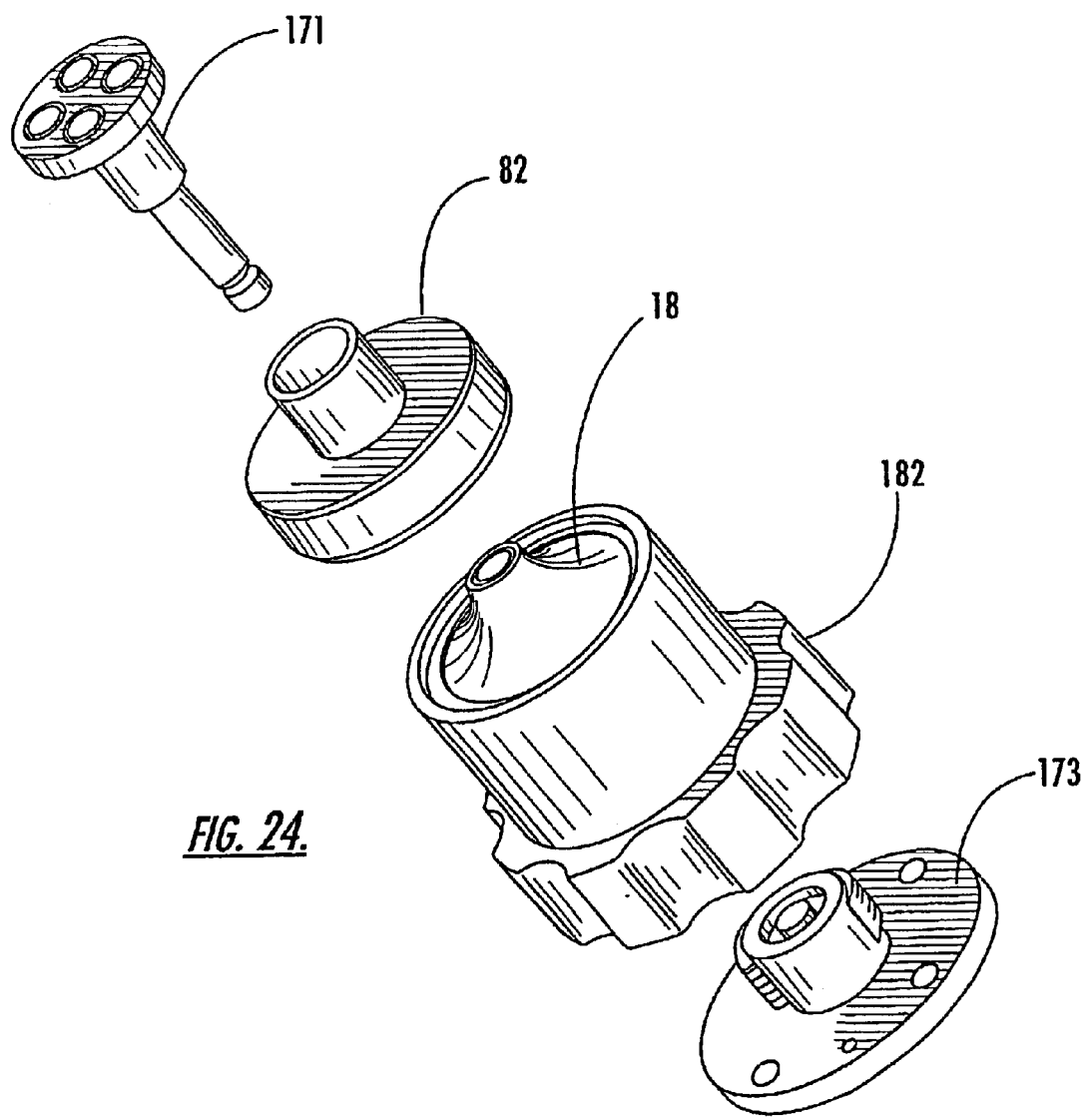
FIG. 24 is an exploded view of an inlet cone fixture and associated inlet cone according to the present invention.
Figure 25:
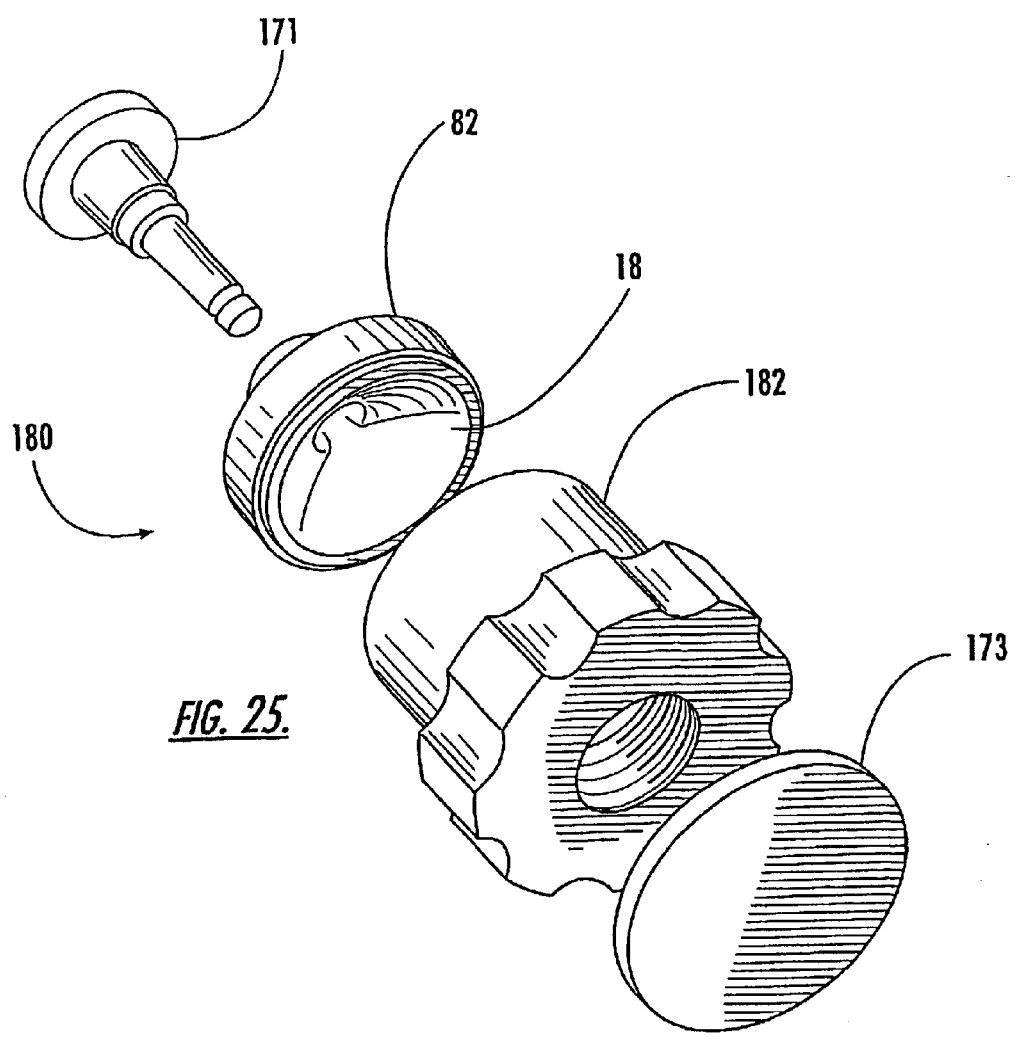
FIG. 25 is another exploded view of the inlet cone fixture and inlet cone of FIG. 24.

Referring to FIGS. 24 and 25, inlet cone fixture 180 is substituted for pre-separator fixture 21 when inlet cone 18 is used in conjunction with the impaction test. Inlet cone fixture 180 includes an inlet cone adaptor 182. Inlet cone 18 is sealed between inlet cone adaptor 182 and cover 82. Cover 82 and inlet cone 18 are mounted to mounting post 171, and inlet cone adaptor 182 is mounted to mounting plate 173.

Referring to FIGS. 26–38, the novel flow-through design and automated operation of workstation W to facilitate drug recovery (i.e., how solvent is introduced to the components containing drug and how the drug is removed) will now be described.

Figure 26:
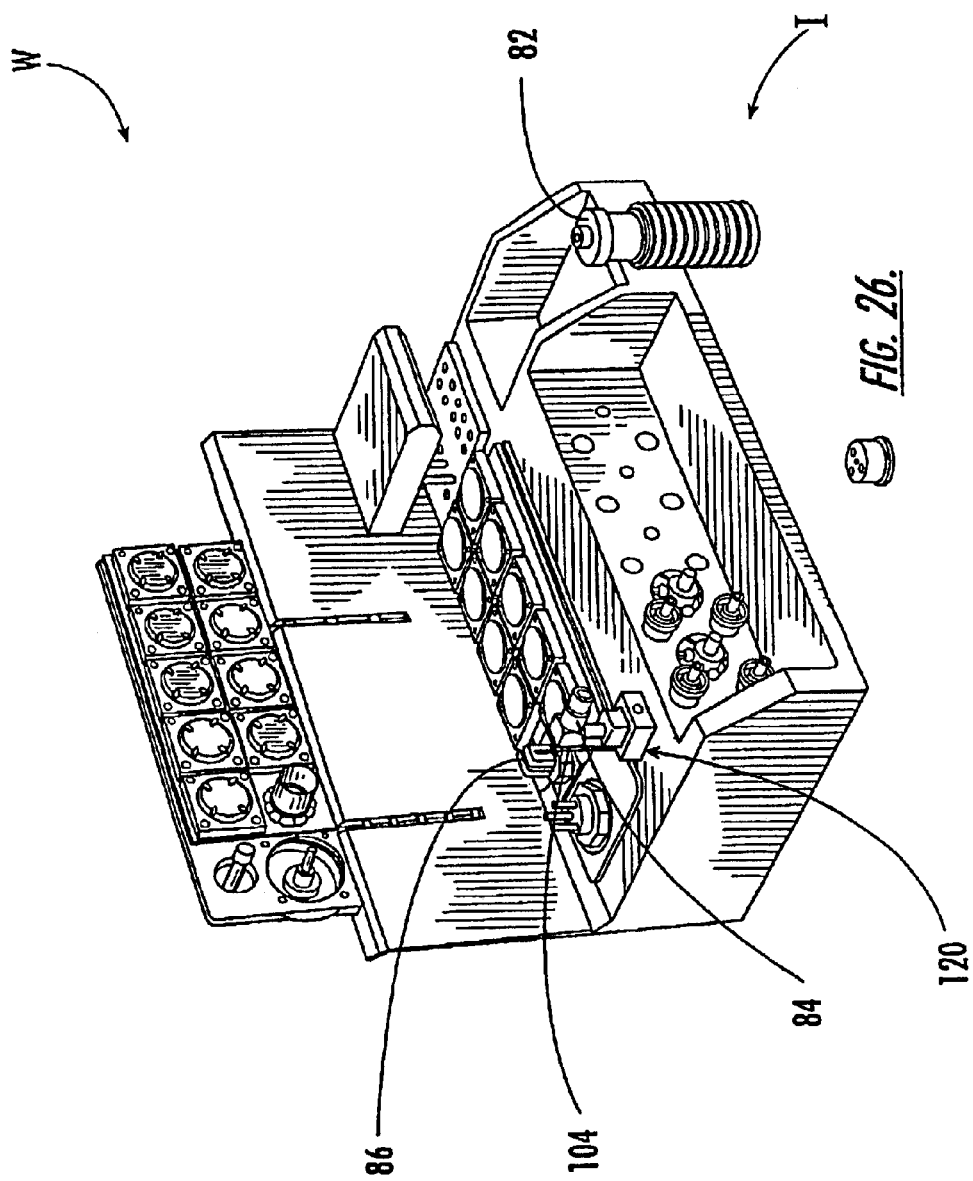
FIGS. 26, 27 and 28 are perspective views of the workstation of FIG. 2 illustrating the process of loading various parts of an impactor unit thereon in accordance with the present invention.
Figure 27:
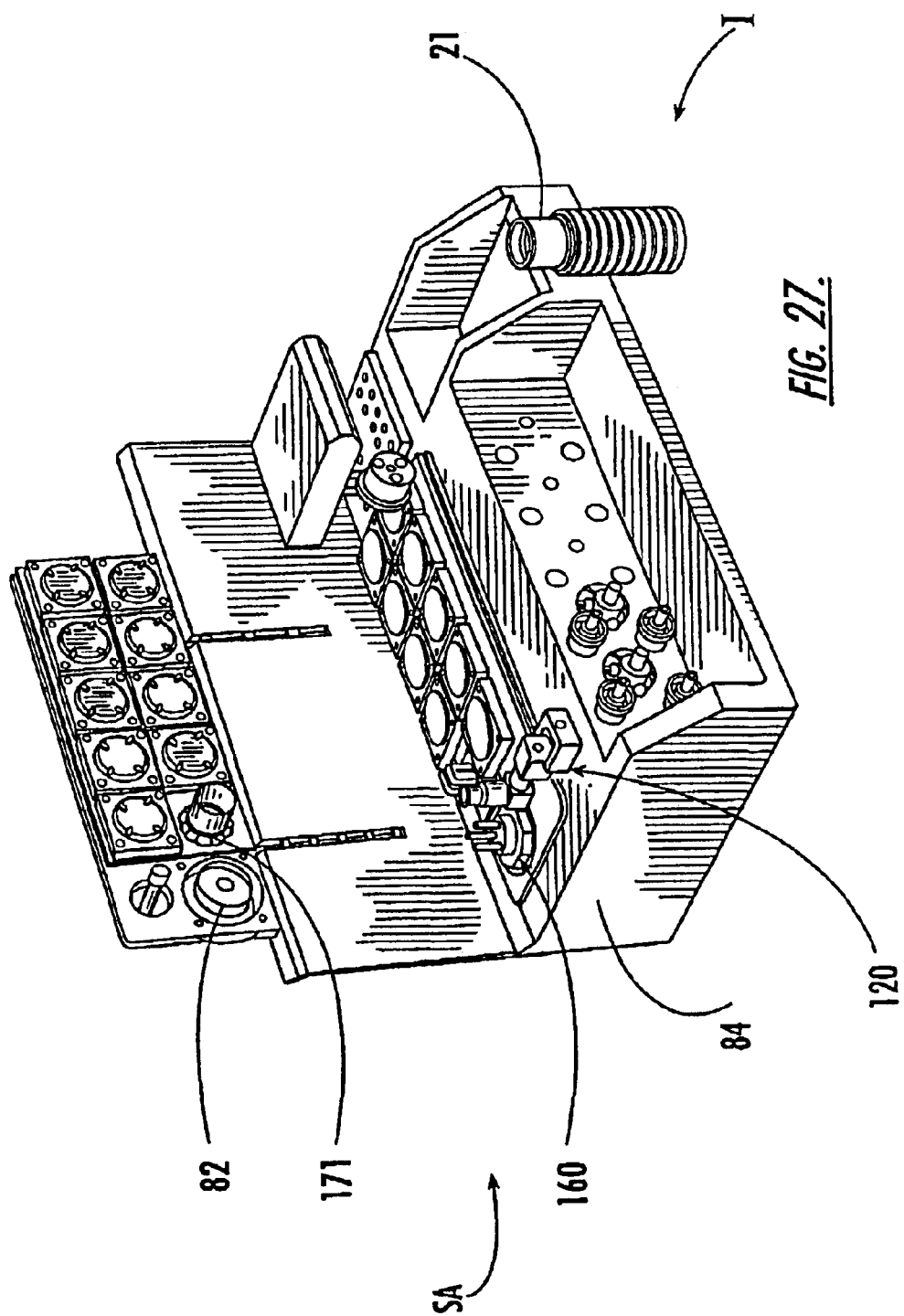
Figure 28:
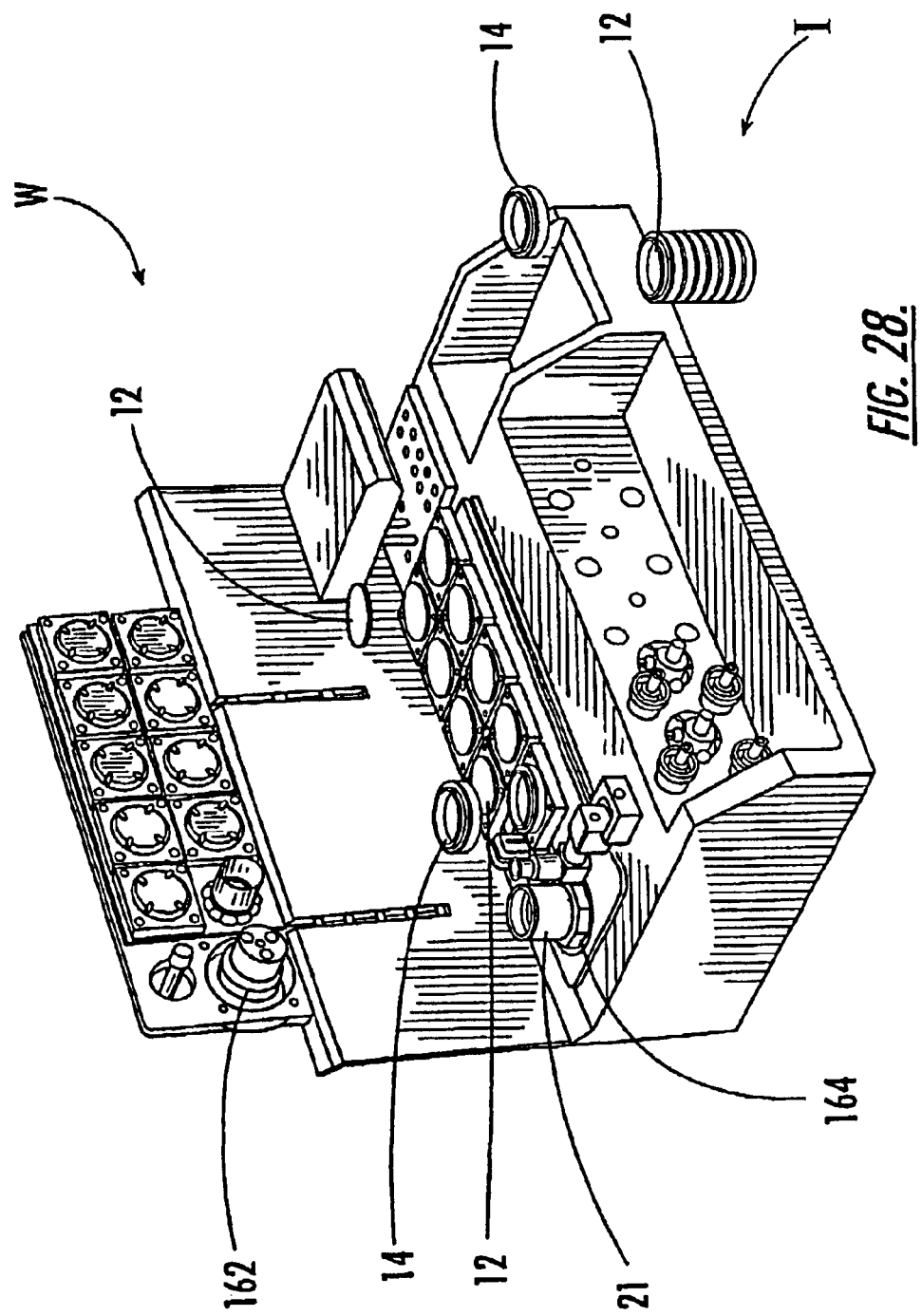

Referring to FIG. 26, after impactor I has been dosed, mouthpiece 86 is removed from impactor I and inserted onto lower mouthpiece adaptor 104. Throat 84 is then removed and inserted onto mounting post 126 of throat fixture 120, which is initially locked in its vertical position. Referring to FIG. 27, throat fixture 120 is unlocked and rotated into its horizontal position such that throat 84 is disposed within the area of sealing assembly SA. Cover 82 is removed from impactor I and inserted onto mounting post 171 of pre-separator fixture 160. Referring to FIG. 28, upper pre-separator adaptor 162 is inserted onto mounting post 171 and pre-separator 21 is removed from impactor I and inserted onto lower pre-separator adaptor 164. FIG. 28 also shows that jet plates 12 and impaction discs 14 of each respective stage ST have begun to be removed from impactor I and placed onto corresponding lower stage adaptors 93.

Figure 29:
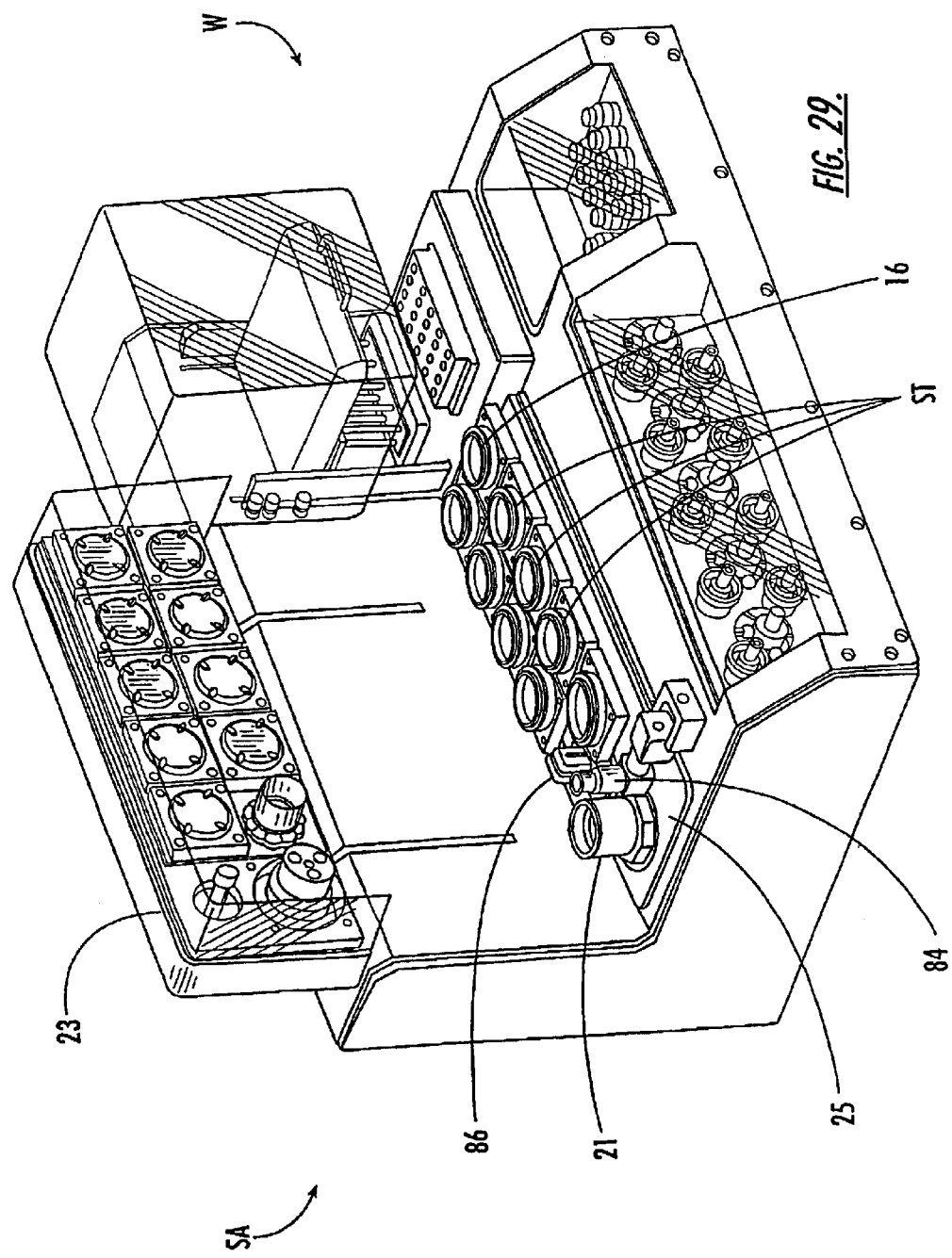
FIGS. 29, 30 and 31 are perspective views of the workstation of FIG. 2 illustrating the operation of a sealing assembly provided therewith in accordance with the present invention.
Figure 30:
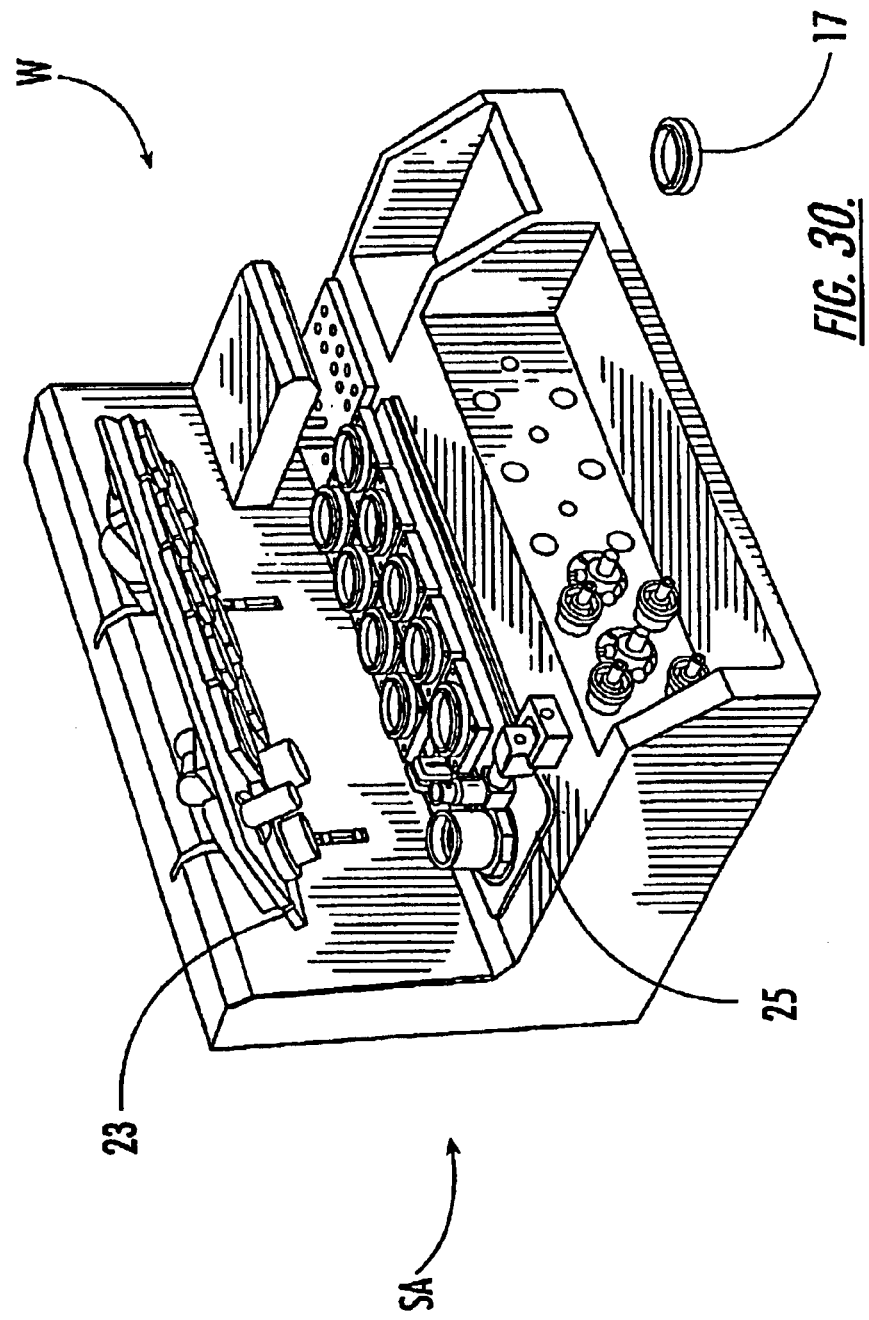

Referring to FIG. 29, impactor I has been completely disassembled and all components containing particles have been loaded onto those portions of fixtures $SF_0$–$SF_7$, FF, 100, 120, and 160 or 180 disposed on lower clamping plate 25. Upper clamping plate 23 is then caused by clamping drive subassembly 30 to move from its open positions shown in FIG. 29, rotate through intermediate positions such as that shown in FIG. 30, and ultimately move to its closed position shown in FIG. 31. Once the closed position of sealing assembly SA is reached, all particle-containing components of impactor I are sealed simultaneously and each fixture $SF_0$–$SF_7$, FF, 100, 120, and 160 or 180 creates a sealed chamber for its associated component. Owing to the design of the various profiles of fixtures $SF_0$–$SF_7$, FF, 100, 120, and 160 or 180, the dead spaces within each impactor component are minimized, which greatly facilitates efficient flow of solvent to the impactor components. In the closed position, the solvent circuit defined by sealing assembly SA, pump and valve system PVS, solvent tube arrangement STA, sampling module SM, and various fluid conduits communicating with these modules, is essentially closed.

Similar to the case of stage and filter fixtures $SF_0$–$SF_7$ and FF wherein springs 99 are provided as shown in FIGS. 11 and 12, other fixtures 100, 120, and 160 or 180 are spring-loaded within sealing assembly SA in order to equalize the clamping force and thereby overcome any machining and operating tolerances and ensure a good seal by fixtures $SF_0$–$SF_7$, FF, 100, 120, and 160 or 180. Thus, for example, springs or other types of biasing members (not shown) are used in mounting upper mounting plate 106 of mouthpiece fixture 100, throat sealing member 148 of throat fixture 120, and mounting post 171 of either pre-separator fixture 160 or inlet cone fixture 180 to upper clamping plate 23.

Figure 31:
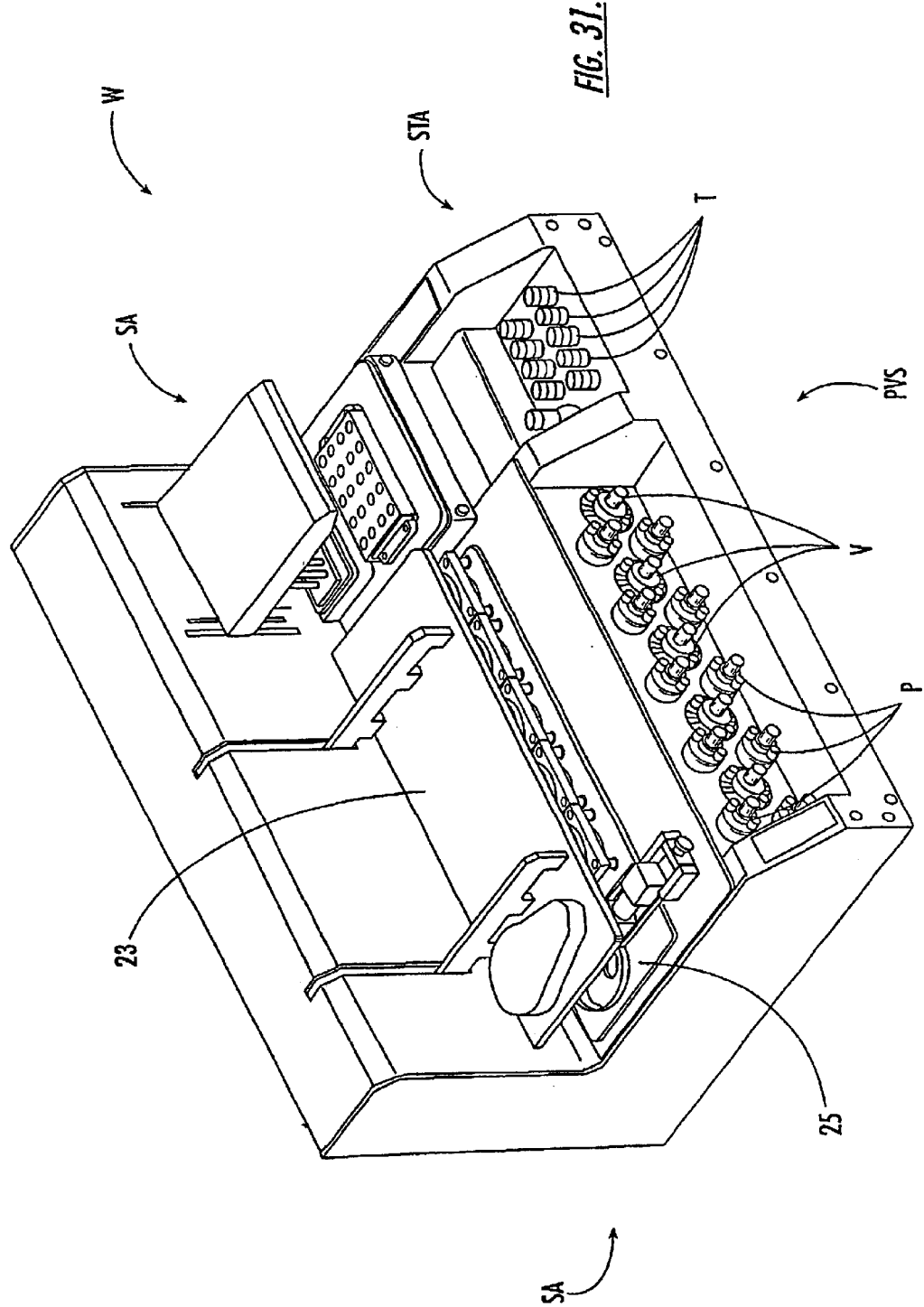
Figure 32:
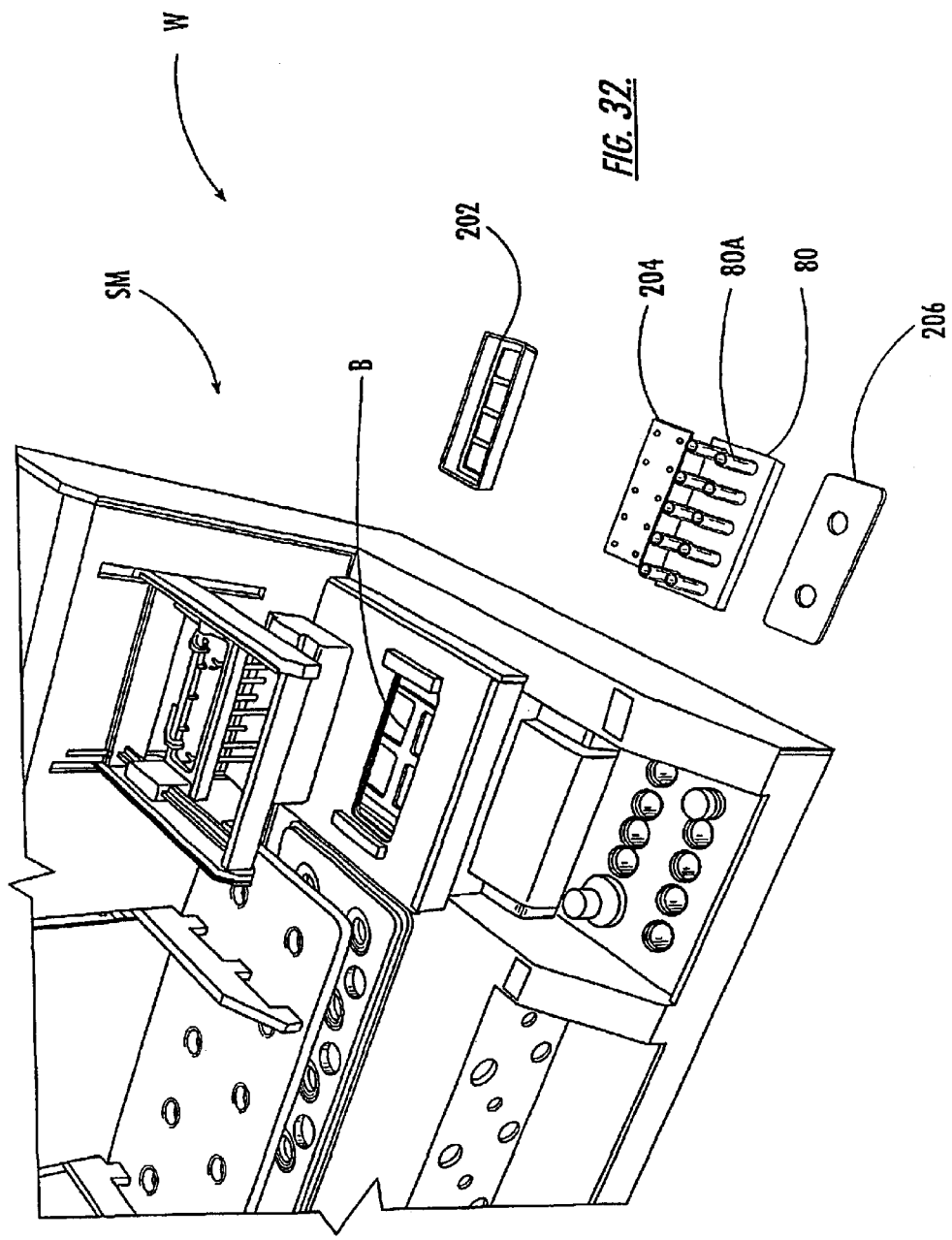
FIGS. 32, 33, 34, 35, 36, 37 and 38 are perspective views of a portion of the workstation of FIG. 2 illustrating the operation of the sampling module provided therewith in accordance with the present invention.

Referring generally to FIG. 31, during the particulate sample recovery process, pumps P are activated to draw metered quantities of solvent from an external solvent reservoir into solvent tubes T. Valves V are then repositioned to form a closed loop system. Pumps P are activated to direct solvent from solvent tubes T into a top portion $SA_1$ (see FIG. 2) of sealing assembly SA. Solvent then flows through sealing assembly SA across the impactor components sealed therein, thereby collecting the particles contained on the various surfaces of the impactor components. The sample-containing solvent then flows through a bottom portion $SA_2$ of sealing assembly SA and is recirculated back through the plumbing system to solvent tubes T. By reconfiguring pumps P and valves V, the sample-containing solvent is directed to sampling module SM.

Figure 36:
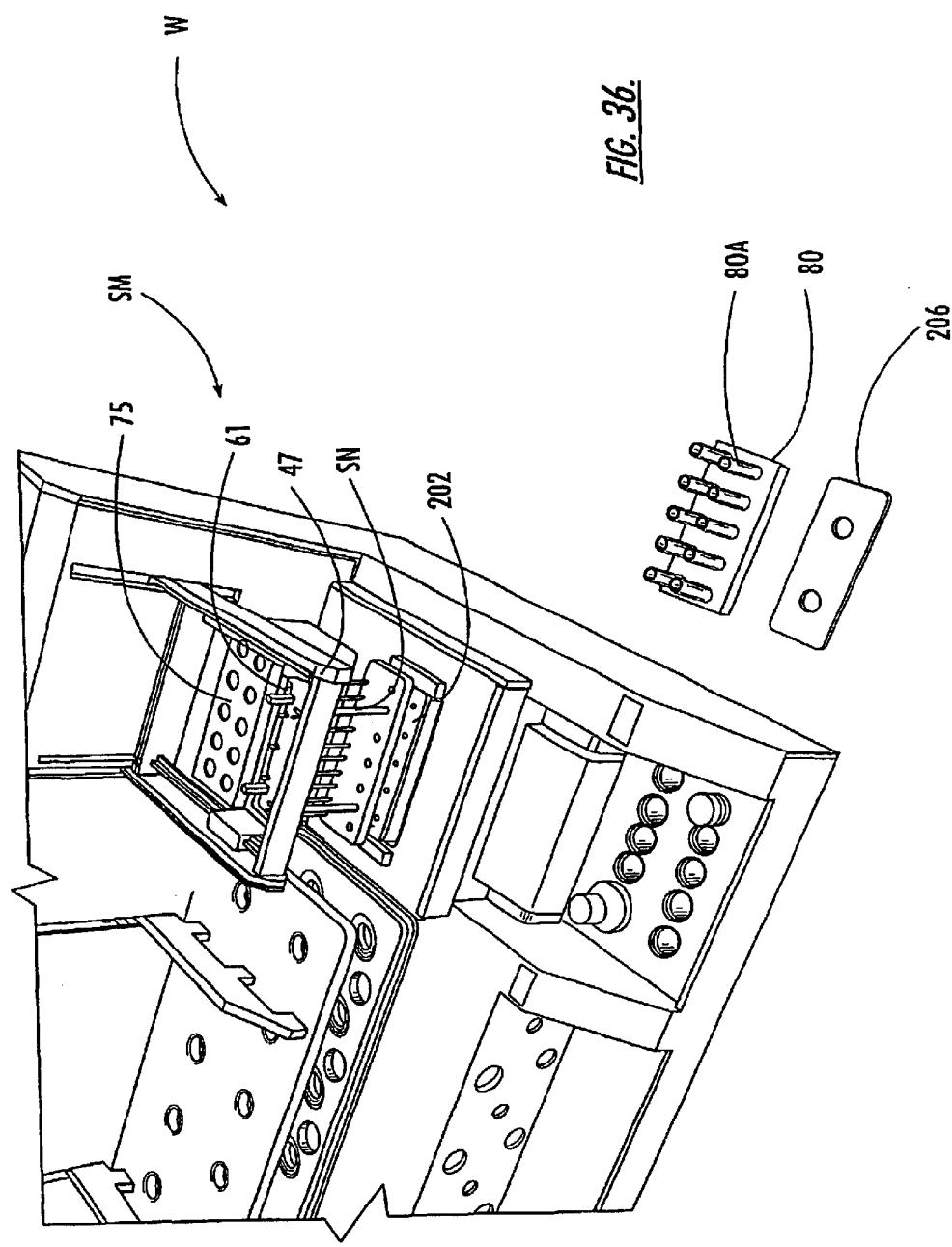

Referring to FIGS. 32–38, the details of sampling module SM will now be described. Sampling module SM includes a novel automated pump calibration system that can be utilized prior to operation of workstation W and initiation of the sample collection process. The pump calibration system incorporates a commercially available laboratory balance B into sampling module SM below the area at which rack 80 is normally positioned, and also includes a detachable solvent reservoir 202 and reservoir cover 204. During the pump calibration procedure, solvent reservoir 202 is filled with solvent and placed onto balance B as shown in FIG. 33 and cover 204 is placed onto reservoir 202 as shown in FIG. 34. Reservoir 202 is weighed. Sampling module SM then causes first and second brackets 47 and 61 to move as shown in FIG. 35 until sampling needles SN are positioned over solvent reservoir 202 as shown in FIG. 36. In sequential manner, each corresponding pump P and sampling needle SN are then caused to draw a volume of solvent, having a quantitative value indicated by pump P or its valve V, out of reservoir 202 and into one of solvent tubes T. Pump P is then stopped and sampling needles SN are pulled out of reservoir 202. Pump P is reversed and sampling needle SN dispenses the volume of solvent back into reservoir 202. Balance B is used in performing gravimetric measurements of the volume of solvent dispensed by each pump P into solvent reservoir 202. If necessary, minor adjustments are made to one or more of pumps P or valves V and the updated information is stored in the system software.

Figure 37:
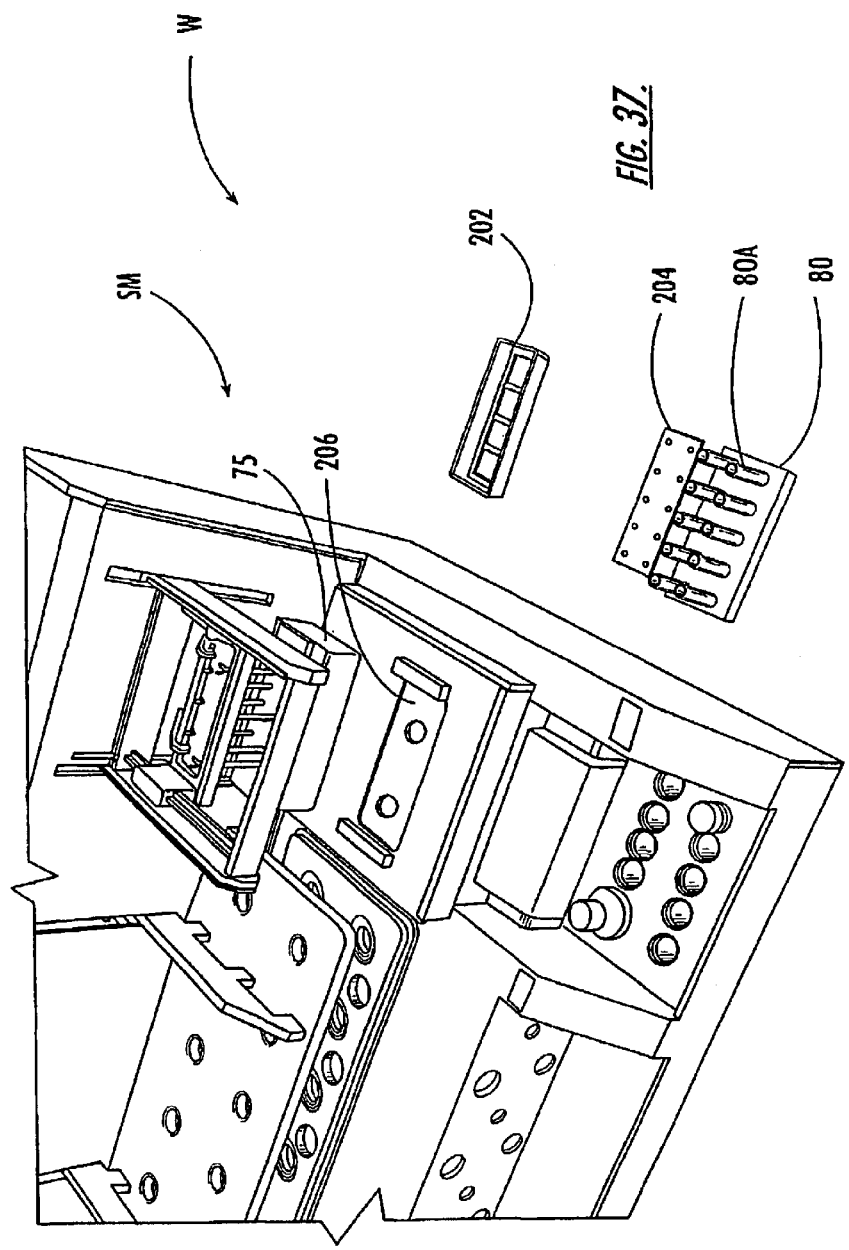
Figure 38:
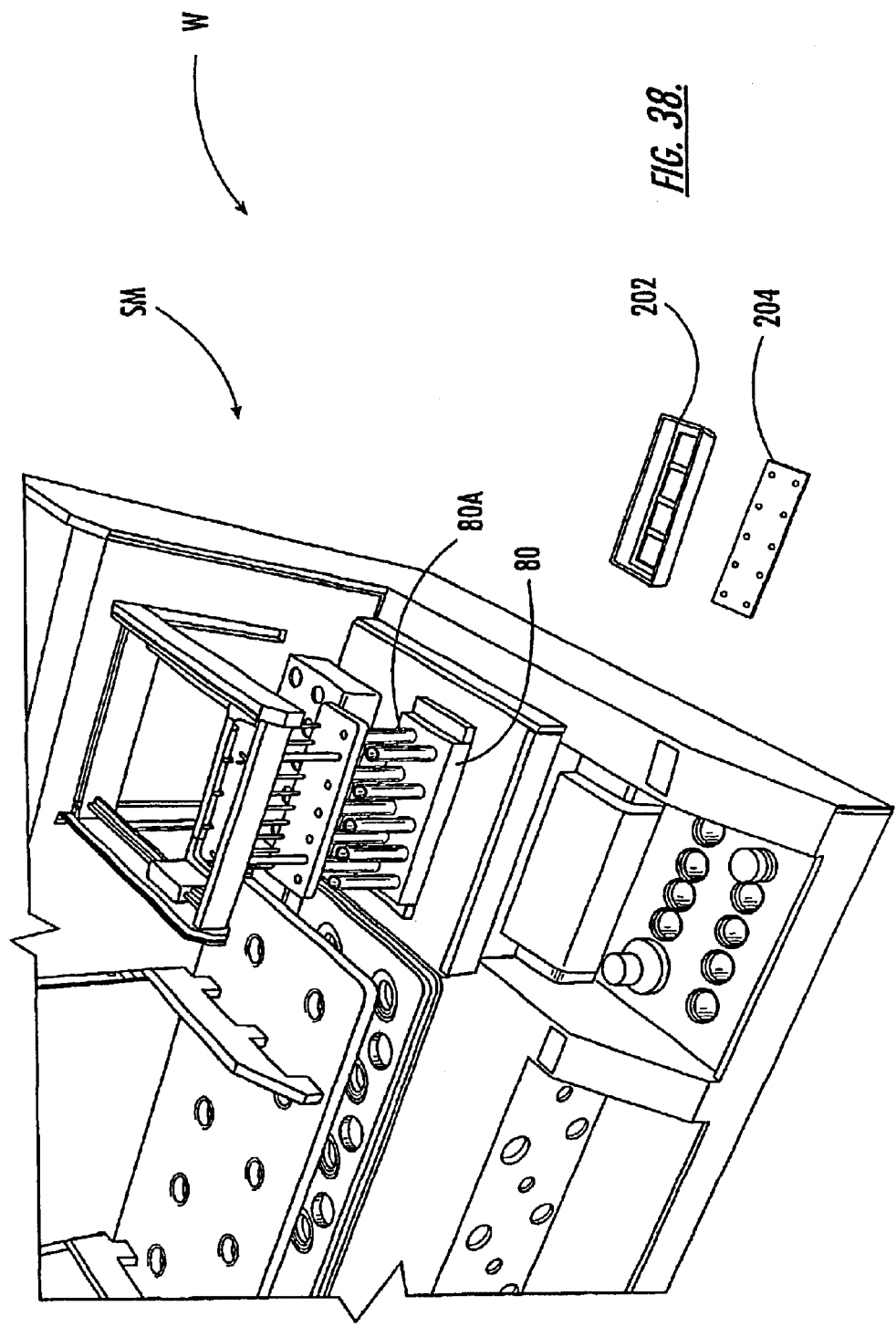

Referring to FIGS. 37 and 38, once the calibration procedure is completed, reservoir 202 and cover 204 are removed from sampling module SM and replaced with a rack mounting plate 206 and rack 80 containing test tubes or vials 80A. Sampling module SM is then used after the sample recovery process to direct pre-programmed quantities of sample-containing solvent into test tubes or vials 80A so that appropriate analysis can be conducted on the samples. The design of sampling module SM permits automated parallel transfer of the sample solutions from each impactor component into collection vials 80A or to waste receptacle 75. Neither the design of the rack 80, the number of sets of collection vials 80A contained on rack 80, nor the size of such vials 80A affects the automated operation of sampling module SM.

It should be noted that, apart from the exemplary embodiment described hereinabove, sealing assembly SA could be modified to adapt to other types of impaction testing equipment. That is, the present invention is not limited to use in conjunction with cascade-type impactors I.

It will be understood that various details of the invention may be changed without departing from the scope of the invention. Furthermore, the foregoing description is for the purpose of illustration only, and not for the purpose of limitation—the invention being defined by the claims.

What is claimed is:

1. An automated sealing assembly for use in an automated sample collection workstation comprising:

(a) a lower clamping plate;

(b) an upper clamping plate movable with respect to the lower clamping plate and adapted for sealable engagement with the lower clamping plate; and (c) a clamping drive assembly including a track plate having a track, an axle support, an axle supported by the axle support, a bracket connected to the upper clamping plate and to the axle, the bracket movably and rotatably supported in the track and pivotable about the axle, a motor, and a drive member powered by the motor and adapted to move the bracket along the track; wherein said automated sealing assembly is present in the automated sample collection workstation.

2. The sealing assembly according to claim 1 further comprising a plurality of fixtures adapted to receive particle-containing components from a particle testing device.

3. The sealing assembly according to claim 2 wherein the fixtures are mounted to the upper and lower clamping plates.

4. The sealing assembly according to claim 3 wherein the fixtures include biasing members.

5. The sealing assembly according to claim 2 wherein the particle-containing components include stages from an impaction testing device.

* * * * *